United States Patent
Xu et al.

(10) Patent No.: US 11,058,399 B2
(45) Date of Patent: Jul. 13, 2021

(54) BUBBLE-INDUCED COLOR DOPPLER FEEDBACK DURING HISTOTRIPSY

(71) Applicant: THE REGENTS OF THE UNIVERSITY OF MICHIGAN, Ann Arbor, MI (US)

(72) Inventors: Zhen Xu, Ann Arbor, MI (US); Ryan M. Miller, Ann Arbor, MI (US); Adam D. Maxwell, Ann Arbor, MI (US); Charles A. Cain, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/713,441

(22) Filed: Sep. 22, 2017

(65) Prior Publication Data
US 2018/0049719 A1   Feb. 22, 2018

Related U.S. Application Data

(63) Continuation of application No. 14/046,024, filed on Oct. 4, 2013, now abandoned.
(Continued)

(51) Int. Cl.
*A61B 8/08* (2006.01)
*A61B 17/22* (2006.01)
(Continued)

(52) U.S. Cl.
CPC .......... *A61B 8/488* (2013.01); *A61B 5/4848* (2013.01); *A61B 8/54* (2013.01);
(Continued)

(58) Field of Classification Search
None
See application file for complete search history.

(56) References Cited

U.S. PATENT DOCUMENTS

| 3,243,497 A | 3/1966 | Kendall et al. |
| 3,679,021 A | 7/1972 | Goldberg et al. |

(Continued)

FOREIGN PATENT DOCUMENTS

| CN | 102481164 A | 5/2012 |
| DE | 3220751 A1 | 12/1983 |

(Continued)

OTHER PUBLICATIONS

Non-invasive Creation of an Atrial Septal Defect by Histotripsy in a Canine Model by Xu et al. pub. Published online Feb. 1, 2010. doi: 10.1161/CIRCULATIONAHA.109.889071.*

(Continued)

*Primary Examiner* — Katherine L Fernandez
*Assistant Examiner* — Michael S Kellogg
(74) *Attorney, Agent, or Firm* — Shay Glenn LLP

(57) ABSTRACT

A Histotripsy therapy system is provided that can include any number of features. In some embodiments, the system includes a high voltage power supply, a pulse generator electrically coupled to at least one signal switching amplifier, at least one matching network electrically coupled to the signal switching amplifier(s), and an ultrasound transducer having at least one transducer element. The Histotripsy therapy system can further include an ultrasound Doppler imaging system. The Doppler imaging system and the Histotripsy therapy system can be synchronized to enable color Doppler acquisition of the fractionation of tissue during Histotripsy therapy. Methods of use are also described.

6 Claims, 16 Drawing Sheets

Related U.S. Application Data

(60) Provisional application No. 61/710,172, filed on Oct. 5, 2012.

(51) Int. Cl.
  *A61B 17/225* (2006.01)
  *A61B 8/00* (2006.01)
  *A61B 5/00* (2006.01)
  *G01S 15/89* (2006.01)

(52) U.S. Cl.
  CPC .... *A61B 17/22012* (2013.01); *A61B 17/2258* (2013.01); *G01S 15/899* (2013.01); *G01S 15/8979* (2013.01); *A61B 5/0035* (2013.01); *A61B 5/0059* (2013.01); *A61B 5/0075* (2013.01); *A61B 8/543* (2013.01); *G01S 15/8981* (2013.01)

(56) References Cited

U.S. PATENT DOCUMENTS

| | | |
|---|---|---|
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,453,408 A | 6/1984 | Clayman |
| 4,483,345 A | 11/1984 | Miwa |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |

(56) References Cited

U.S. PATENT DOCUMENTS

| | | |
|---|---|---|
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 10,046,181 B2 | 8/2018 | Barthe et al. |
| 10,058,352 B2 | 8/2018 | Carvell et al. |
| 10,130,828 B2 | 11/2018 | Vortman et al. |
| 10,912,463 B2 | 2/2021 | Davies et al. |
| 10,973,419 B2 | 4/2021 | Corl |
| 10,993,618 B2 | 5/2021 | Mansker et al. |
| 2001/0039420 A1 | 11/2001 | Burbank et al. |
| 2001/0041163 A1 | 11/2001 | Sugita |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0234438 A1 | 10/2005 | Mast et al. |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0033417 A1 | 2/2008 | Nields et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319356 A1* | 12/2008 | Cain ............... A61B 17/22004 601/2 |
| 2008/0319376 A1 | 12/2008 | Wilcox et al. |

(56) References Cited

U.S. PATENT DOCUMENTS

| | | |
|---|---|---|
| 2009/0030339 A1 | 1/2009 | Cheng et al. |
| 2009/0112098 A1 | 4/2009 | Vaezy et al. |
| 2009/0177085 A1* | 7/2009 | Maxwell .......... A61B 17/22004 600/439 |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0287083 A1 | 11/2009 | Kushculey et al. |
| 2010/0011845 A1 | 1/2010 | Laugharn et al. |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0054315 A1 | 3/2011 | Roberts et al. |
| 2011/0054363 A1 | 3/2011 | Cain et al. |
| 2011/0112400 A1 | 5/2011 | Emery et al. |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0251528 A1 | 10/2011 | Canney et al. |
| 2011/0257524 A1 | 10/2011 | Gertner |
| 2011/0263967 A1 | 10/2011 | Bailey et al. |
| 2012/0029353 A1 | 2/2012 | Slayton et al. |
| 2012/0059264 A1* | 3/2012 | Hope Simpson ........ A61B 8/06 600/454 |
| 2012/0059285 A1 | 3/2012 | Soltani et al. |
| 2012/0092724 A1 | 4/2012 | Pettis |
| 2012/0130288 A1 | 5/2012 | Holland et al. |
| 2012/0136279 A1 | 5/2012 | Tanaka et al. |
| 2012/0172720 A1 | 7/2012 | Asami et al. |
| 2012/0189998 A1 | 7/2012 | Kruecker et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0190623 A1 | 7/2013 | Bertolina et al. |
| 2013/0303906 A1 | 11/2013 | Cain et al. |
| 2014/0058293 A1 | 2/2014 | Hynynen et al. |
| 2014/0073995 A1 | 3/2014 | Teofilovic et al. |
| 2014/0074076 A1 | 3/2014 | Gertner |
| 2014/0100459 A1 | 4/2014 | Xu et al. |
| 2014/0128734 A1 | 5/2014 | Genstler et al. |
| 2014/0200489 A1 | 7/2014 | Behar et al. |
| 2014/0330124 A1 | 11/2014 | Carol |
| 2015/0011916 A1 | 1/2015 | Cannata et al. |
| 2015/0151141 A1 | 6/2015 | Arnal et al. |
| 2015/0258352 A1 | 9/2015 | Lin et al. |
| 2015/0375015 A1 | 12/2015 | Cain |
| 2016/0135916 A1 | 5/2016 | Rakic et al. |
| 2016/0151618 A1 | 6/2016 | Powers et al. |
| 2016/0184614 A1 | 6/2016 | Matula et al. |
| 2016/0184616 A1 | 6/2016 | Cain et al. |
| 2016/0206867 A1 | 7/2016 | Hossack et al. |
| 2016/0287909 A1 | 10/2016 | Maxwell et al. |
| 2018/0154186 A1 | 6/2018 | Xu et al. |

FOREIGN PATENT DOCUMENTS

| | | |
|---|---|---|
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| EP | 2887989 B1 | 2/2021 |
| EP | 2802276 B1 | 4/2021 |
| EP | 2809221 B1 | 4/2021 |
| GB | 2099582 A | 12/1982 |
| JP | 60-80779 A | 5/1985 |
| JP | 61-196718 A | 8/1986 |
| JP | 02-215451 A | 8/1990 |
| JP | 06-197907 A | 7/1994 |
| JP | 07-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | 10-512477 A | 12/1998 |
| JP | 2000300559 A | 10/2000 |
| JP | 2003510159 A | 3/2003 |
| JP | 2004505660 A | 2/2004 |
| JP | 2005167058 A | 6/2005 |
| JP | 2007144225 A | 6/2007 |
| JP | 2007520307 A | 7/2007 |
| JP | 2010019554 A | 1/2010 |
| JP | 2010029650 A | 2/2010 |
| JP | 2010204068 A | 9/2010 |
| JP | 2004512502 A | 4/2014 |
| WO | WO94/06355 A1 | 3/1994 |
| WO | WO02/32506 A1 | 4/2002 |
| WO | WO2005/018469 A1 | 3/2005 |
| WO | WO2008/051484 A2 | 5/2008 |
| WO | WO2011/040054 A1 | 7/2011 |
| WO | WO2011/092683 A1 | 8/2011 |
| WO | WO2011/154654 A2 | 12/2011 |
| WO | WO2014/071386 A1 | 5/2014 |
| WO | WO2015/000953 A1 | 1/2015 |

OTHER PUBLICATIONS

Investigation of the Mechanism of ARFI-based Color Doppler Feedback of Histotripsy Tissue Fractionation by Miller et al. pub. Ultrasonics Symposium (IUS), 2013 IEEE International, Issue Date: Jul. 21-25, 2013.*

Medical ultrasound by Wikipedia pub. online on Sep. 30, 2012 at https://en.wikipedia.org/w/index.php?title=Medical_ultrasound &oldid=515340960.*

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemy; vol. 11(1); pp. 39-42; Jan. 2004.

Arani et al.; Transurethral prostate magnetic resonance elestography; prospective imaging requirements; Magn. Reson. Med.; 65(2); pp. 340-349; Feb. 2011.

Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.

Atchley et al.; Thresholds for cavitation produced in water by pulsed ultrasound; Ultrasonics.; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Avago Technologies; Avago's ACNV2601 optocoupler is an optically coupled logic gate; Data Sheet; 2 pages; Jul. 29, 2010.

(56) References Cited

OTHER PUBLICATIONS

Avtech; AVR-8 Data sheet; May 23, 2004; 3 pages; retrieved from the internet (http//www.avtechpulse.com).
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14: Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vase Intery Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Hartmann; Ultrasonic properties of poly(4-methyl pentene-1), Journal of Applied Physics, vol. 51, pp. 310-314, Jan. 1980.

Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (year of pub. sufficiently earlier than effective US filing date and any foreign priority date)1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.

(56) References Cited

OTHER PUBLICATIONS

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

Miller et al.; Real-time elastography-based monitoring of histotripsy tissue fractionation using color doppler; Ultrasonics Symposium (IUS); 2012 IEEE International; 8 pages; Oct. 7-10, 2012.

Nightingale et al.; Analysis of contrast in images generated with transient acoustic radiation force; Ultrasound Med Biol; 32(1); pp. 61-72; Jan. 2006.

Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.

Okada et al.; A case of hepatocellular carcinoma treated by MR-guided focused ultrasound ablation with respiratory gating; Magn Reson Med Sci; 5(3); pp. 167-171; Oct. 2006.

Palmeri et at.; Acoustic radiation force-based elasticity imaging methods; Interface Focus; 1; pp. 553-564; Aug. 2011.

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.

Parsons et al.; Pulsed cavitational ultrasound therapy for controlled tissue homogenization; Ultrasound in Med. & Biol.; vol. 32(1); pp. 115-129; Jan. 2006.

Pishchalnikov et al.; Cavitation Bubble Cluster Activity in the Breakage of Kidney Stones by Lithotripter Shock Waves; J Endourol.; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.

Rosenschein et al.; Ultrasound Imaging-Guided Noninvasive Ultrasound Thrombolysis: Preclinical Results; Circulation; vol. 102; pp. 238-245, Jul. 11, 2000.

Rowland et al.; MRI study of hepatic tumours following high intensity focused ultrasound surgery; British Journal of Radiology; 70; pp. 144-153; Feb. 1997.

Roy et al.; A precise technique for the measurement of acoustic cavitation thresholds and some preliminary results; Journal of the Acoustical Society of America; vol. 78(5); pp. 1799-1805; Nov. 1985.

Sapareto et al.; Thermal dose determination in cancer therapy; Int J Radiat Oncol Biol Phys; 10(6); pp. 787-800; Apr. 1984.

Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

Sato et al.; Experimental Investigation of Phased Array Using Tapered Matching Layers. 2002 IEEE Ultrasound Symposium. vol. 2; pp. 1235-1238, Oct. 2002.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

Song et al; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).

Souchon et al.; Visualisation of HIFU lesions using elastography of the human prostate in vivo: Preliminary results; Ultrasound Med. Biol; 29(7); pp. 1007-1015; Jul. 2003.

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument) Jul. 2011.

TODA; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.*, A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy'Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Hall et al.; U.S. Appl. No. 15/583,852 entitled "Method of manufacturing an ultrasound system," filed May 1, 2017.

\* cited by examiner

BUBBLE-INDUCED COLOR DOPPLER FEEDBACK DURING HISTOTRIPSY

CROSS REFERENCE TO RELATED APPLICATIONS

This application is a continuation of U.S. application Ser. No. 14/046,024, filed Oct. 4, 2013, which application claims the benefit under 35 U.S.C. 119 of U.S. Provisional Application No. 61/710,172, filed Oct. 5, 2012, titled "Real-Time Elastography-Based Feedback During Histotripsy", which applications are incorporated by reference as if fully set forth herein.

GOVERNMENT INTEREST

This invention was made with Government support under EB008998, awarded by the National Institutes of Health. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to applying therapeutic ultrasound to tissue. More specifically, this disclosure relates to real-time Doppler-based feedback during Histotripsy therapy to tissue.

BACKGROUND

Imaging feedback during treatment is essential for ensuring high accuracy and safety of minimally invasive and non-invasive ablation therapies. Radiofrequency ablation (RFA) is currently the standard local ablation therapy. No imaging feedback is typically used to monitor RFA treatment. The treatment completion is usually determined by calculation of the delivered thermal dose necessary to destroy all cells within a treated volume. However, accurate dose calculation is nearly impossible to achieve. MRI-based thermometry is being investigated for RFA monitoring, but this technique requires an open magnet MRI system, which is not clinically available.

High intensity focused ultrasound (HIFU) thermal therapy is a relatively new and promising non-invasive ablation technology. Currently HIFU systems mostly use MRI thermometry to monitor the thermal dose during treatment, but the use of MRI for such long procedures is expensive. As a state of art imaging feedback for HIFU, MRI thermometry measures the temperature change in the tissue to derive the treatment tissue effect, but not the direct change in the tissue. In addition to MR thermometry, ultrasound and MRI elastography and other ultrasound-based feedback have also been investigated to monitor the tissue elasticity increase produced by the HIFU treatment.

Histotripsy is a new non-invasive and non-thermal ultrasound ablation technology. It uses high intensity, microsecond-long ultrasound pulses to control cavitating bubble clouds for tissue fractionation. In some embodiments, generating Histotripsy pulses comprises generating short (<20 μsec), high pressure (peak negative pressure >10 MPa) shockwave ultrasound pulses at a duty cycle <5%. The Histotripsy-induced cavitation cloud can be monitored through ultrasound imaging and provides an inherent feedback for targeting. The tissue fractionation induced by Histotripsy appears as a dark zone on B-mode ultrasound images due to speckle amplitude reduction, although significant speckle reduction is only observed when substantial tissue fractionation is generated. It is also difficult to identify a level of backscatter amplitude reduction corresponding to complete tissue fractionation or a specific fractionation level corresponding to complete tissue death, due to the variation in speckle amplitude across different tissue samples.

As the tissue elasticity decreases with increasing fractionation, Histotripsy tissue fractionation can also be monitored using ultrasound elastography. Ultrasound elastography can detect the elasticity decrease in the fractionated tissue and shows a higher sensitivity to monitor the early stage tissue fractionation compared to speckle amplitude reduction. Unlike conventional ultrasound imaging that portrays the difference in acoustic impedance of the tissue, ultrasound elastography measures the difference in tissue stiffness. The tissue stiffness can be described by an elastic modulus, which can be measured by the tissue's resistance to deformation, in compression/tension (Young's modulus) or in shear (shear modulus). Tissue deformation occurs in response to a stress being applied to the tissue. The stress can be applied by a manual push from the clinician's finger or imaging probe. It can also be applied by acoustic radiation force from an ultrasound pulse. The dynamic displacement response of the soft tissue is typically monitored using cross-correlation between adjacent ultrasound image frames of the displayed tissue. The amplitude and temporal characteristics of the displacement, including peak displacement, time to peak displacement, and tissue velocity, can then be extracted and used to calculate the elastic modulus of the tissue.

Current elastography methods require relatively large processing times compared to the pulse frequency of ultrasound therapy such as Histotripsy. These processing times can be from a fraction of a second to several seconds in length, which cannot be obtained simultaneously with the application of several to a thousand Histotripsy pulses a second.

SUMMARY

In some embodiments, generating Histotripsy pulses comprises generating short (<20 μsec), high pressure (peak negative pressure >10 MPa) shockwave ultrasound pulses at a duty cycle <5%.

An ultrasound system configured to monitor bubble-induced color Doppler during Histotripsy treatment is provided, comprising a ultrasound therapy transducer configured to transmit Histotripsy pulses into tissue having a pulse length less than 20 μsec, a peak negative pressure greater than 10 MPa, and a duty cycle less than 5%, an ultrasound Doppler imaging system configured to transmit ultrasound imaging pulses along the propagation direction of the Histotripsy pulses and generate color Doppler imaging of the tissue from the transmitted ultrasound imaging pulses, and a control system configured to synchronize transmission of the ultrasound imaging pulses with transmission of the Histotripsy pulses to monitor Histotripsy tissue fractionation in real-time with the Doppler imaging.

In some embodiments, the control system is configured to set specific Doppler parameters to follow the tissue displacement using color Doppler, such as a time delay between a Doppler pulse packet and the Histotripsy pulses, a pulse repetition frequency of the Doppler pulse packet, and a number of frames in the Doppler pulse packet.

In one embodiment, the ultrasound therapy transducer includes a central hole configured to house an ultrasound imaging transducer of the ultrasound Doppler imaging system so as to align the ultrasound imaging transducer along a propagation path of the Histotripsy pulses.

In another embodiment, the control system is configured to synchronize transmission of the ultrasound imaging pulses with transmission of the Histotripsy pulses by sending a trigger signal from the control system to the ultrasound Doppler imaging system during the transmission of each Histotripsy pulse plus a predetermined time delay.

In some embodiments, a pulse repetition frequency (PRF) and a number of frames of Doppler imaging are set by the ultrasound Doppler imaging system so color Doppler flow velocity increases as a degree of tissue fractionation generated by the Histotripsy pulses increases.

In another embodiment, an expansion of a temporal profile of a color Doppler velocity increases as a degree of tissue fractionation generated by the Histotripsy pulses increases.

In some embodiments, a rapid expansion of a temporal profile of a color Doppler velocity corresponds to microscopic cellular damage, while a slow expansion of the temporal profile of the color Doppler velocity corresponds to macroscopic tissue structural damage generated by the Histotripsy pulses.

In one embodiment, a saturation or decrease of expansion of a temporal profile of a color Doppler velocity indicates complete homogenization and liquefaction of the tissue.

In some embodiments, a PRF and number of frames of color Doppler imaging is controlled by the ultrasound Doppler imaging system such that a direction of a color Doppler flow changes from towards an imaging transducer to away from the imaging transducer when the tissue is sufficiently fractionated by the Histotripsy pulses.

In one embodiment, a wall filter value can be set by the ultrasound Doppler imaging system such that a color Doppler flow map matches the tissue when it has been fractionated by the Histotripsy pulses.

In some embodiments, 2D or 3D images of the tissue can be reconstructed by scanning a focus of the ultrasound therapy transducer and collecting a color Doppler map at a position of the focus.

In other embodiments, the Doppler imaging can be configured to monitor vessel function and cardiac function during the transmission of Histotripsy pulses.

In some embodiments, the ultrasound Doppler imaging system can display different colors to distinguish tissue motion from blood flow.

A method of monitoring Doppler-based feedback during Histotripsy treatment is provided, comprising the steps of transmitting Histotripsy pulses into tissue having a pulse length less than 20 μsec, a peak negative pressure greater than 10 MPa, and a duty cycle less than 5% with an ultrasound therapy transducer, obtaining color Doppler acquisition of the tissue during transmission of the Histotripsy pulses with an ultrasound imaging system, and synchronizing the color Doppler acquisition with the transmission of Histotripsy pulses with a control system.

In some embodiments, the method comprises setting specific Doppler parameters to follow tissue displacement using color Doppler acquisition.

In other embodiments, the method comprises obtaining color Doppler acquisition along a propagation line of the Histotripsy pulses to measure tissue displacement of the tissue.

In one embodiment, the synchronizing step comprises sending a trigger signal to the ultrasound imaging system from the control system during the transmission of each Histotripsy pulse plus a predetermined time delay.

In another embodiment, the method comprises setting a PRF and number of frames for color Doppler acquisition such that a color Doppler flow velocity increases with an increasing degree of tissue fractionation generated by the Histotripsy pulses.

In some embodiments, the method comprises setting a PRF and number of frames for color Doppler acquisition such that a direction of a color Doppler flow changes from towards the ultrasound imaging system to away from the ultrasound imaging system when the tissue is sufficiently fractionated by the Histotripsy pulses.

In another embodiment, the method comprises setting a wall filter value such that a color Doppler flow map matches a fractionated tissue region generated by the Histotripsy pulses.

In some embodiments, the method comprises reconstructing 2D or 3D Doppler imaging of a fractionated tissue by scanning a focus of the ultrasound therapy system and collecting a color Doppler map at a position of the focus.

In other embodiments, the method comprises monitoring vessel function and cardiac function during transmission of the Histotripsy pulses.

In some embodiments, the method comprises distinguishing tissue displacement from blood flow with the color Doppler acquisition.

In other embodiments, the color Doppler acquisition can be used to monitor and indicate microscopic cellular damage versus macroscopic tissue structure homogenization.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
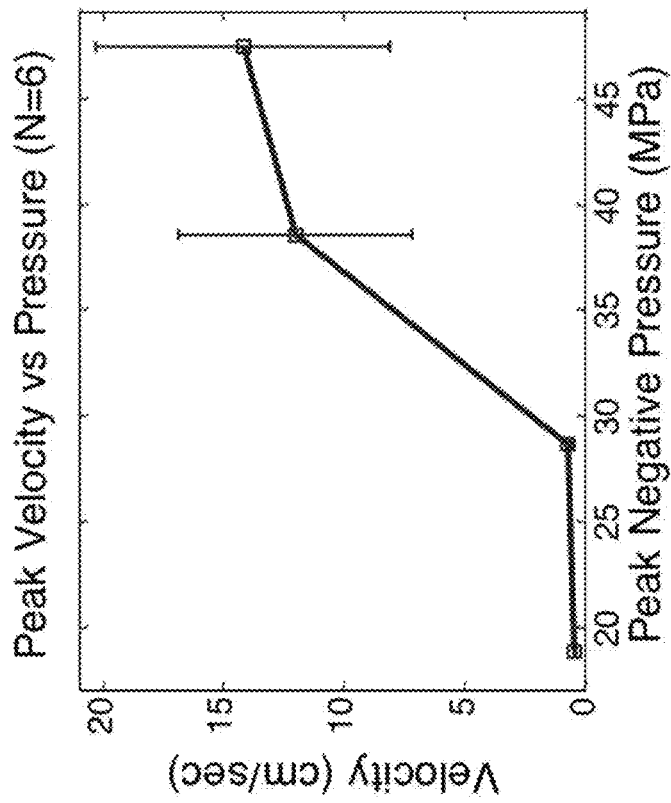
FIGS. 1A-1B: Velocity observed at the therapy focus following Histotripsy pulses of various focal pressures (left), along with a plot of the average peak velocity observed for each of the tested pressures (right) within the focal region in the agarose phantom using particle image velocimetry (PIV). Without cavitation generated by the Histotripsy pulse, no appreciable motion was detected. When cavitation occurred, the peak motion detected by PIV increased with increasing Histotripsy pulse pressure.

This disclosure introduces new imaging feedback systems and methods using bubble-induced color Doppler to monitor the Histotrispy-induced tissue fractionation in real-time. This novel approach can monitor the level of tissue fractionation generated by Histotripsy with improved sensitivity compared to backscatter speckle amplitude reduction and can be implemented in real-time during Histotripsy treatment. Further areas of applicability will become apparent from the description provided herein. The description and specific examples in this summary are intended for purposes of illustration only and are not intended to limit the scope of the present disclosure.

Example embodiments will now be described more fully with reference to the accompanying drawings. Embodiments are provided so that this disclosure will be thorough, and will fully convey the scope to those who are skilled in the art. Numerous specific details are set forth such as examples of specific components, devices, and methods, to provide a thorough understanding of embodiments of the present disclosure.

In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In this disclosure, an innovative bubble-induced Color Doppler approach is described to monitor Histotripsy fractionation in real-time.

When a cavitation cloud is generated in tissue by a Histotripsy pulse, substantial motion is induced in the focal zone and observable on color Doppler synchronized with the Histotripsy pulse. Without cavitation, the motion is negligible.

Figure 1B:
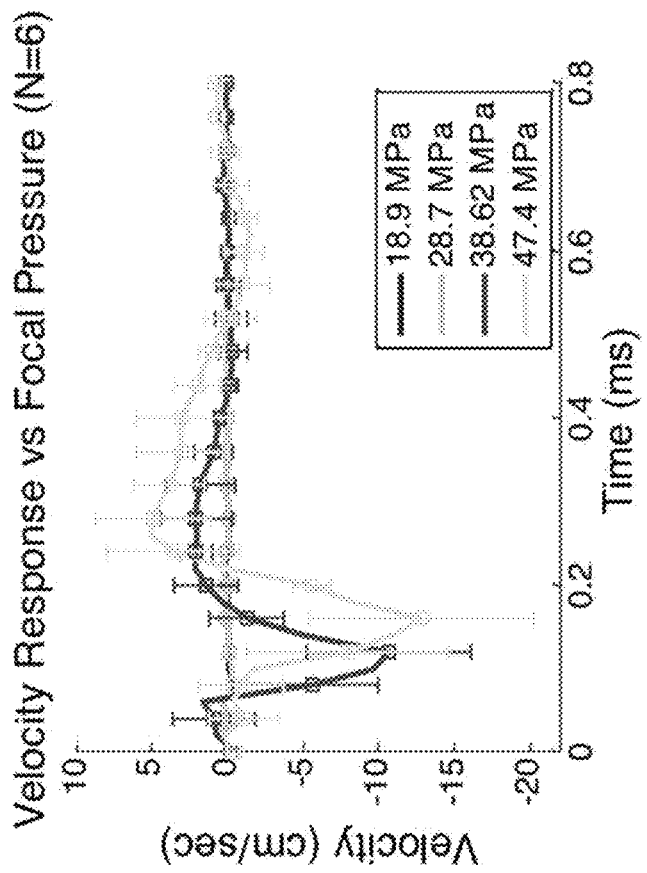

To measure the motion of the focal volume exposed to Histotripsy, an experiment was conducted in transparent agarose hydrogel tissue mimicking phantom with a thin layer (<1 mm) of glass beads with an 8-12 micron mean diameter. The motion in the focal volume exposed to Histotripsy was measured by tracking the motion of the glass beads using high-speed images and particle image velocimetry (PIV). This phantom was treated with 2-cycle pulses at estimated peak negative pressures of 18.9-47.4 MPa using a 500 kHz transducer. This transducer is composed of 32 elements with 50 mm diameter mounted confocally on a 15 cm hemispherical shell. High speed optical images of the focal region were captured for the 20 ms following a single Histotripsy pulse delivered. Measurable motion was detected only when the focal pressure was sufficient to produce a cavitation bubble cloud. FIGS. 1A-1B show a plot of the average velocity profile after each Histotripsy pulse along with the average peak velocity observed for each of the tested focal pressures. FIG. 1A illustrates the velocity observed at the therapy focus following Histotripsy pulses of various focal pressures, and FIG. 1B shows a plot of the average peak velocity observed for each of the tested pressures within the focal region in the agarose phantom using particle image velocimetry (PIV). Without cavitation generated by the Histotripsy pulse, no appreciable motion was detected. When cavitation occurred, the peak motion detected by PIV increased with increasing Histotripsy pulse pressure.

Following a Histotripsy pulse, a cavitation bubble cloud was generated immediately and collapsed within 300 µS. Residual bubble, nuclei persist for over 100 ms after the cavitation collapse and were clearly visible in high-speed optical images of the focal region after a Histotripsy therapy pulse.

In FIGS. 2A-2D, PIV velocity maps showed 2 phases of motion during the 19 ms after a Histotripsy therapy pulse. For up to the first 2 ms, chaotic motion was present, where the motion was pointed in all directions in a random manner through this period. This chaotic motion phase likely resulted from the violent collapse of the Histotripsy bubble cloud. After this chaotic motion subsides, a coherent motion along the direction of the therapy ultrasound beam was visible. The coherent motion was first moving away from the therapy transducer for up to 6 ms, and then rebounding back towards the therapy transducer through the remaining 19 ms. This coherent motion may be due to the bubble cloud being pushed by the radiation force of the Histotripsy pulse against an elastic tissue boundary or the asymmetric collapse of the cavitation cloud against the boundary. FIGS. 2A-2D show images of an example progression of the focal region PIV velocity map after the tissue had been treated with 50 Histotripsy pulses. The therapy pulse was propagated from right to left.

Figure 2A:
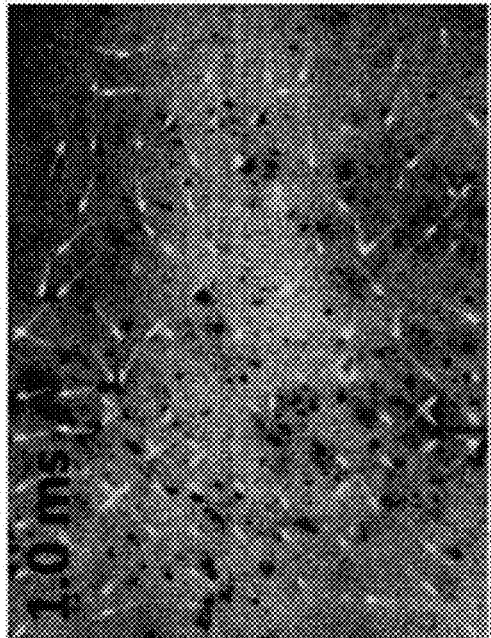
FIGS. 2A-2D: High speed images of the focal region 50 pulses into treatment (therapy applied from the right) with PIV velocity map overlays showing the Histotripsy bubble cloud (top left), chaotic motion immediately after the collapse of the bubble cloud (top right), and finally coherent motion, including a push away from the transducer (bottom left) and subsequent rebound (bottom right).
Figure 2B:
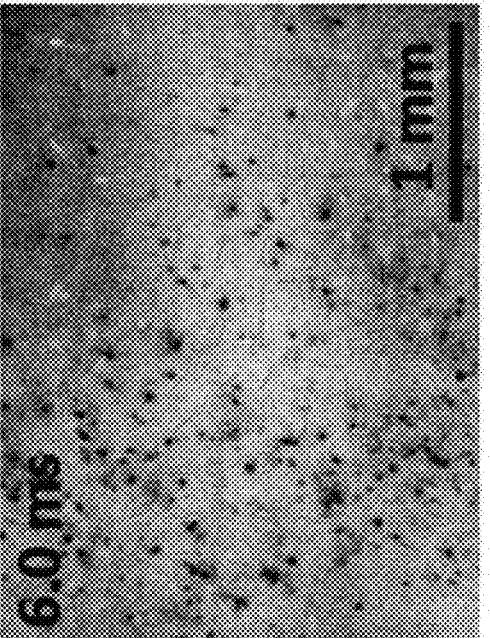
Figure 2C:
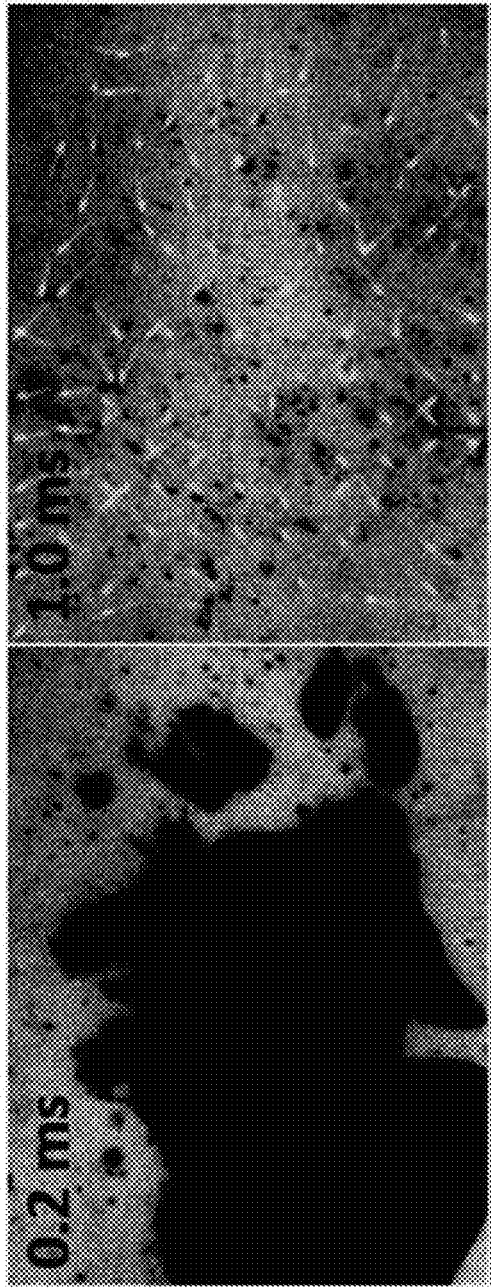
Figure 2D:

In FIGS. 2A-2D, high speed images of the focal region are shown approximately 50 pulses into treatment (therapy applied from the right on the page) with PIV velocity map overlays showing the Histotripsy bubble cloud (FIG. 2A), chaotic motion immediately after the collapse of the bubble cloud (FIG. 2B), and finally coherent motion, including a push away from the transducer (FIG. 2C) and subsequent rebound (FIG. 2D).

The time profile of the resulting velocity of the coherent motion expands as the tissue is fractionated and saturate when the tissue is completely liquefied. Similarly, the averaged velocity within a specific time window of the coherent motion increases with increasing degree of tissue fractionation, and saturates when the clot is completely liquefied.

The velocity resulting from the coherent motion can be detected by ultrasound color Doppler that uses the cross-correlation time/phase lag of adjacent frames to detect the target motion. By synchronizing Doppler pulses with Histotripsy pulses and choosing appropriate parameters, color Doppler can be used to monitor the coherent motion in the Histotripsy treatment region. By choosing the appropriate delay between the Histotripsy pulse and the color Doppler pulse packet, color Doppler can be used to monitor the coherent motion phase without the interference from the chaotic motion. The Doppler velocity can be then analyzed to quantitatively predict the level tissue fractionation during the treatment in real-time. The Doppler velocity map can also be displayed it as a colored region overlaid on the gray-scale image, providing real-time imaging feedback to monitor Histotripsy tissue fractionation. B-Flow and M-mode approaches are possible alternatives to color Doppler.

Figure 3:
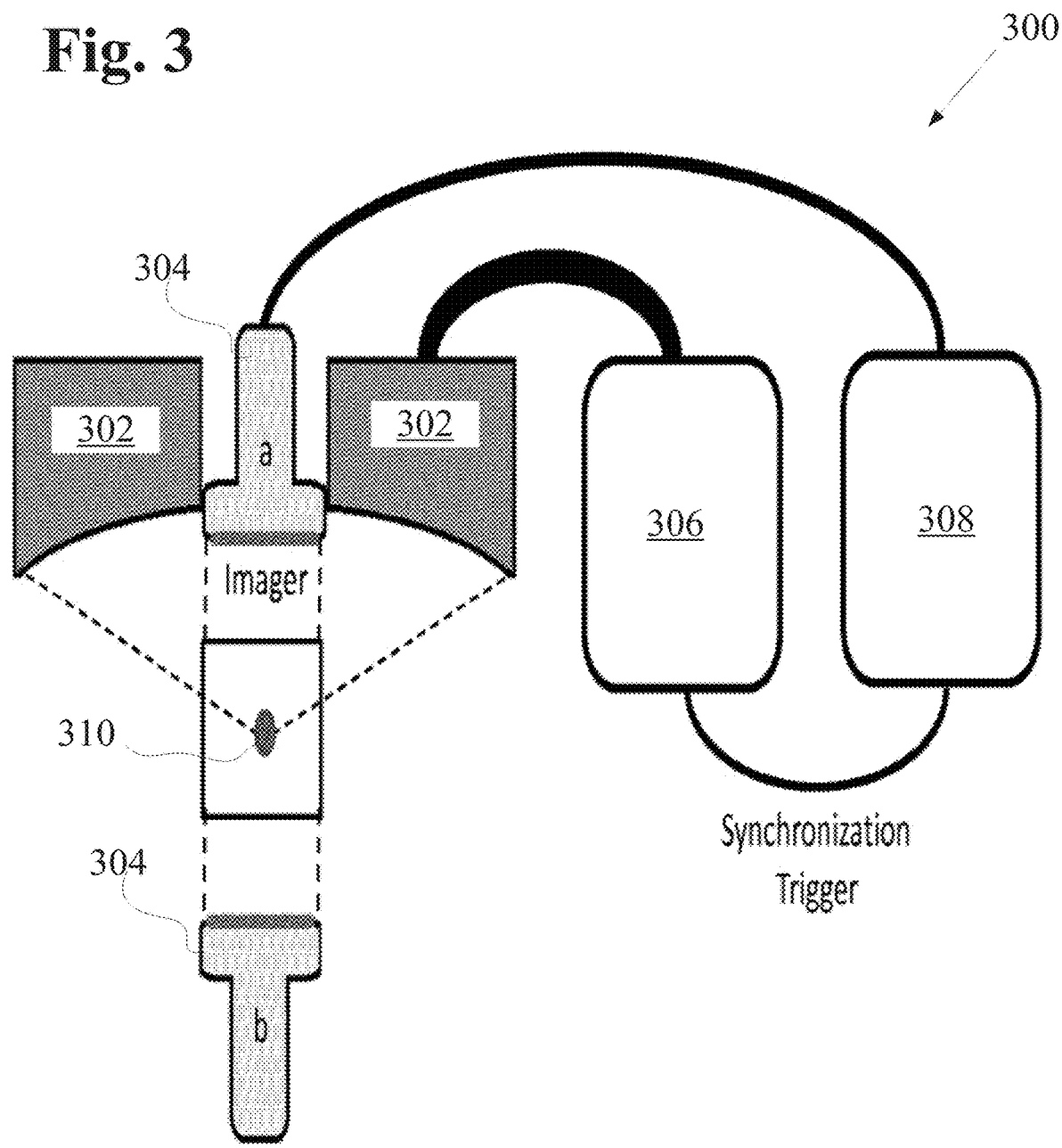
FIG. 3 describes the setup of the Histotripsy system and ultrasound imaging system to perform the bubble-induced color Doppler feedback for Histotripsy treatment.

To perform bubble-induced color Doppler monitoring of Histotripsy, a Histotripsy system (including an ultrasound therapy transducer and associated driving electronics) and an ultrasound imaging system are required. FIG. 3 illustrates a Doppler monitoring Histotripsy system 300 including an ultrasound therapy transducer 302, a Doppler imaging transducer or transducers 304 (shown as 304a and 304b), Histotripsy therapy driving hardware 306 (which can include, for example, a pulse generator, amplifiers, matching networks, and an electronic controller configured to generate Histotripsy pulses in the ultrasound therapy transducer), and imaging hardware 308 which can control Doppler imaging with the Doppler imaging transducer(s) 304. As shown in FIG. 3, the Doppler imaging transducers can be disposed within a cut-out or hole within the ultrasound therapy transducer, for example, so as to facilitate imaging of a focus 310 (and thus the bubble cloud) of the therapy transducer.

After application of the Histotripsy pulse, the tissue velocity along the axial direction or the propagation direction of the ultrasound pulse is monitored using color Doppler. This can be achieved by placing the ultrasound imaging transducer in-line with the therapy transducer, for example, the Histotripsy therapy transducer can have a central hole to house the ultrasound imaging transducer to ensure the imaging transducer is monitoring the axial displacement of the tissue along the propagation direction of the Histotripsy pulse.

The synchronization of the Histotripsy system and Doppler acquisition of the ultrasound imaging system is essential and can be achieved by triggering Doppler pulse transmission from the Doppler imaging transducer(s) using a signal sent out from the Histotripsy therapy driving hardware 306 at an appropriate delay time (negative or positive) after the transmission of the Histotripsy pulse. It is also possible to trigger the Histotripsy therapy driving hardware with a signal from the imaging hardware 308.

Figure 4:
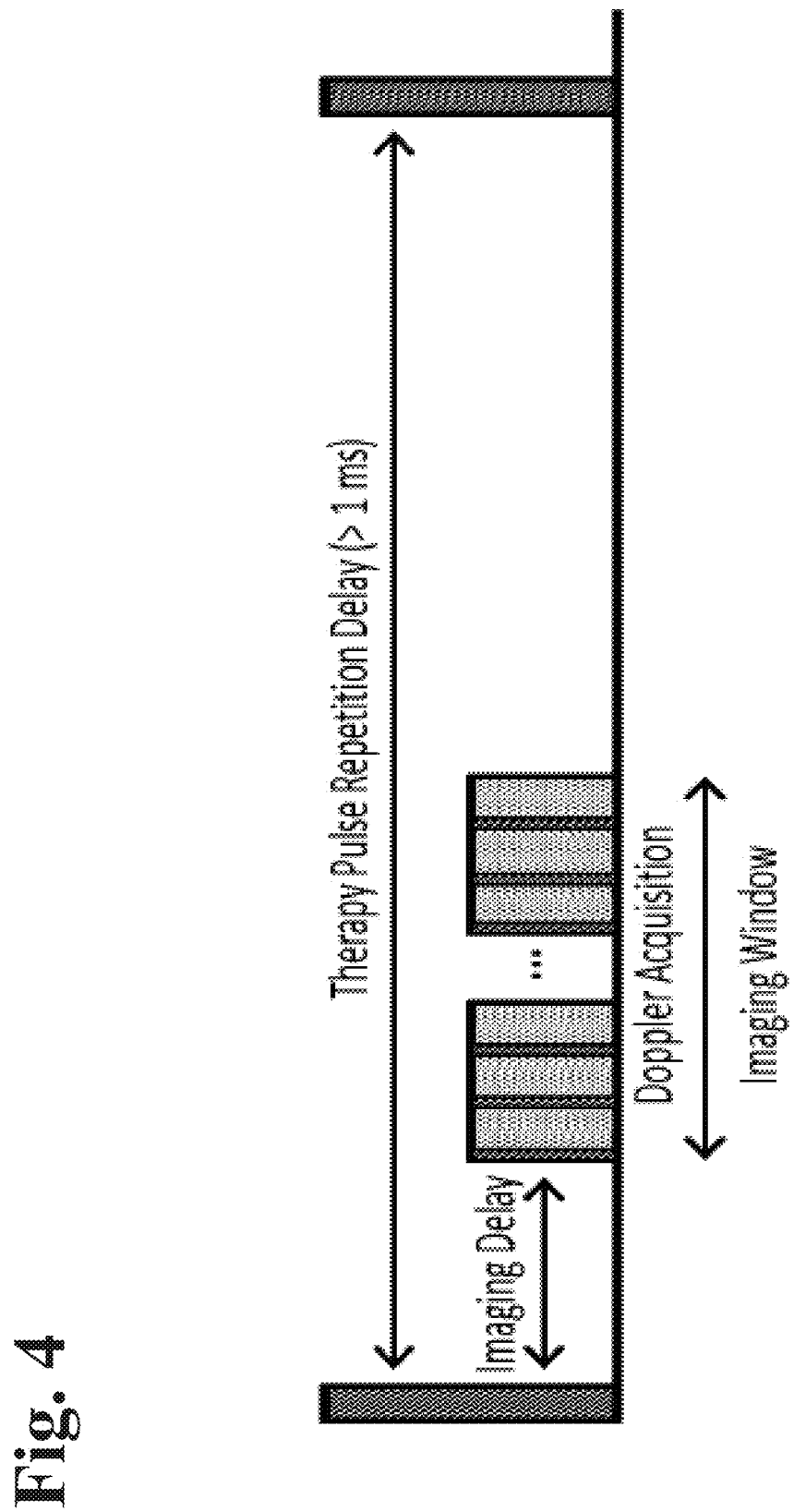
FIG. 4 demonstrates one synchronization scheme to trigger the Doppler pulse transmission and acquisition using a signal sent out from the Histotripsy system at an appropriate delay time (negative or positive) after the transmission of the Histotripsy pulse.

FIG. 4 demonstrates a synchronization scheme according to one embodiment. An appropriate delay needs to be set between the Histotripsy pulse and the Doppler pulse transmission, such that the Doppler velocity measures the coherent motion phase, not the chaotic motion immediately following the Histotripsy pulse. The chaotic motion phase ranges from 300 us to 2 ms, depending on the tissue type and the level of tissue fractionation.

We have treated ex vivo porcine liver tissue using Histotripsy, and compared the bubble-induced color Doppler feedback with the histology of the treated tissue. The histology results show that the temporal profile of the bubble-induced Doppler feedback may be used to predict the microscopic cellular damage versus the macroscopic tissue structure damage. Microscopic cellular damage is sufficient to result in cell death. Microscopic cellular damage to most cells within the treatment region occurs very early on in the Histotrispy treatment, only requiring ~50 pulses. Complete homogenization of tissue structure takes more than 500 pulses.

Correspondingly, the time profile of the Doppler velocity expanded with a very steep slope for the first 50 pulses. After that, the expansion of the temporal profile of the Doppler was much more gradual, until at 900 pulses, the expansion saturates. These results suggest that the bubble-induced color Doppler can be used to monitor and indicate microscopic cellular damage (i.e., cell death) versus macroscopic tissue structure homogenization (i.e., tissue liquefaction). Current B-mode ultrasound imaging is not sensitive enough to monitor the microscopic cellular damage alone. The bubble-induced color Doppler has improved sensitivity to detect the microscopic cellular death as well as damage to the macroscopic tissue structure. This improved sensitivity can dramatically increase the treatment efficiency. Using such increased sensitivity, treatment completion can be determined in real-time for different clinical applications. For example, macroscopic tissue liquefaction is needed for clot removal, while cell death may be sufficient for tumor treatment and benign lesions. This feature is innovative and of clinical importance, and is not available for any current feedback techniques.

The amplitude of bubble-induced color Doppler changes over the Histotripsy treatment may vary across different organs and patients. Our data suggest that the slope or the rate of Doppler velocity change, either the temporal profile of the velocity within sub-time window of the coherent motion, can be used to monitor the treatment, to detect microscopic cellular damage as well as macroscopic tissue structure homogenization. Therefore, the detection does not depend on the absolute value of the Doppler velocity, but the relative change, and therefore is expected to be consistent and reliable across different organs and patients.

Moreover, the Doppler parameters, such as the pulse repetition frequency (PRF) and number of frames for each Doppler acquisition, can be selected appropriately to achieve the desired correlation between the Doppler velocity increase with the increasing degree of tissue fractionation (i.e., Histotripsy treatment progress) in different tissue types. In addition, by setting the wall filter threshold to exceed the background displacement, the color Doppler velocity map region can precisely match the fractionation region.

Further, Doppler parameters (e.g., time window of the Doppler acquisition) can be adjusted, such that the average Doppler velocity is towards the transducer prior to treatment completion shown as one color (e.g., blue), while the Doppler flow is away from the transducer at the treatment completion viewed as a different color (e.g., red). Such a definitive indication for treatment completion is apparent to even inexperienced users. This can be achieved because the temporal profiles of the coherent motion away from the transducer and back towards the transducer expand with the degree of tissue fractionation.

As the residual bubble nuclei from the cavitation bubble cloud collapse generated by Histotripsy lasts over a hundred milliseconds after each Histotripsy pulse and moves with the target tissue, these residual nuclei provide bright speckle to track the bubble-induced motion in the tissue during Histotripsy treatment. They provide strong speckles for displacement the motion tracking, even with poor imaging quality.

Moreover, since Doppler is an essential tool for monitoring cardiovascular function, the capability of color Doppler during Histotripsy treatment allows us to monitor the vessel and cardiac function during the treatment, which could have significant clinical implications. For example, Histotripsy can be used to remove blood clots in the vessel and color Doppler can evaluate whether the blood flow is restored or improved during the Histotripsy treatment in a previously completely or partially occluded vessel.

Histotripsy has also been studied to create a flow channel through the atrial septum between the two atria in the heart for patients with congenital heart disease. In this situation, color Doppler can indicate the generation of the flow channel, i.e., treatment completion. In another example, when treating diseased tissues (such as liver tumor or renal tumor) surrounding major blood vessels, color Doppler can be used to ensure no penetration is generated to the vessel during the Histotripsy treatment. Different colors can be used for bubble-induced color Doppler feedback during Histotripsy (e.g., green and yellow) to distinguish from blue and red commonly used in color Doppler for blood flow.

The bubble-induced color Doppler cannot be used directly to form an image of a large volume, as the Histotripsy pulse is used to treat one focal volume at a time. It is possible to steer the therapy transducer focus (electronically or mechanically) over the large ablated volume and collect the data to reconstruct the 2D/3D image of the ablated volume.

The ablated tissue coagulates quickly after treatment, which may change the elasticity of the treated volume after treatment. If bubble-induced color Doppler will be used for post-treatment lesion evaluation when the tissue is coagulated, we can develop a quick ablation scan sequence to re-fractionate the coagulative tissue prior to the elastography measurement.

To allow simultaneous optical and acoustic interrogation of the focal volume over the course of Histotripsy treatment on a large volume, an experiment was conducted in an acoustically and optically transparent agarose hydrogel tissue mimicking phantom without the addition of any acoustic or optical contrast agents. In this case, a layer of contrast agents would be destroyed or dispersed into the surrounding regions as the focal volume was fractionated by Histotripsy therapy.

Figure 5:
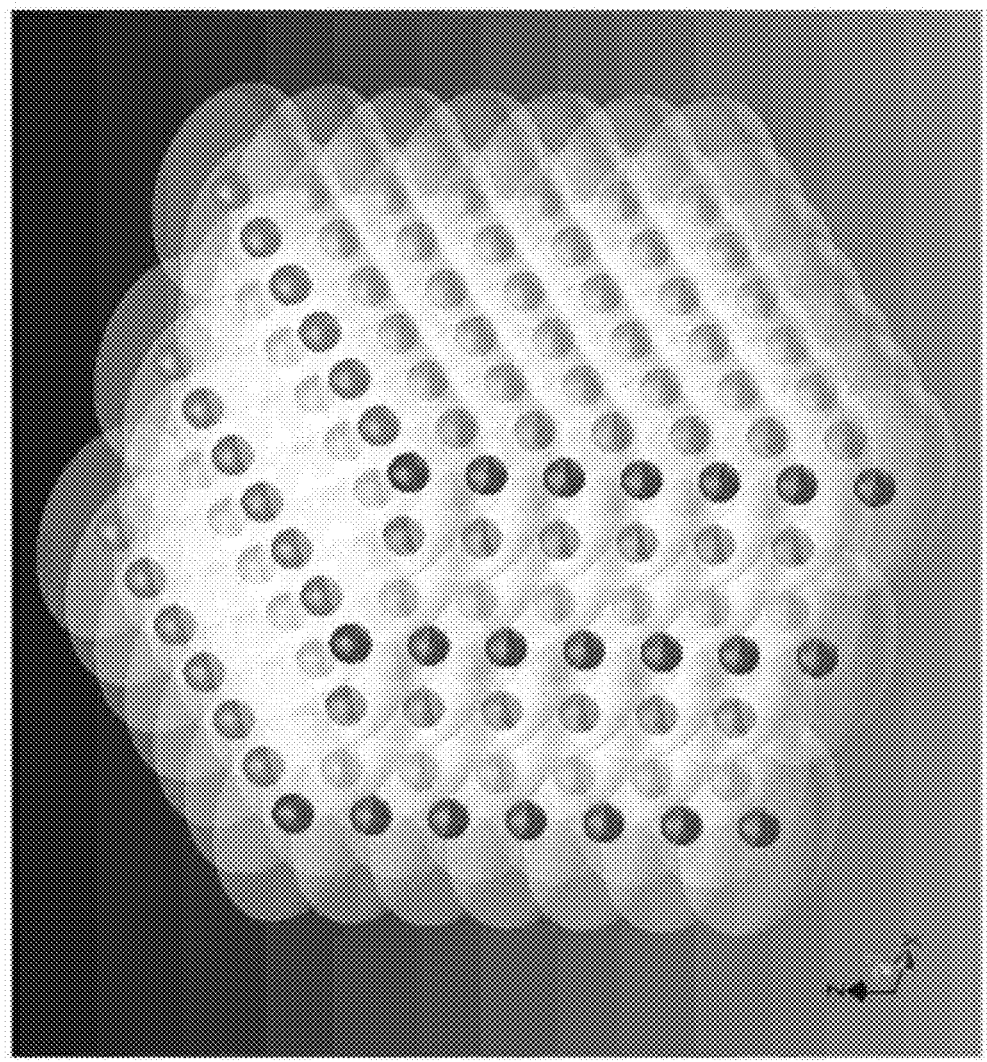
FIG. 5: Steered focal locations for the 219 foci with alternating 1 mm spaced grids of 7×7 foci and 6×6 foci. The axial layers are separated by 1 mm, but with the 6×6 grids offset laterally from the 7×7 layers by 0.5 mm

This phantom was treated with 2-cycle pulses at >50 MPa over a 6 mm cube using the same 500 kHz phased array transducer. This high pressure guaranteed the generation of a cavitation cloud, and the residual bubble nuclei left after its collapse for optical and acoustic contrast at the focal location. To ensure uniform fractionation over the target volume, 219 focal points at 1 mm separations (FIG. 5) were treated sequentially at 150 Hz with a single pulse applied at each location. This process was repeated every 1.5 seconds until all focal locations had been treated with 960 pulses each. This pulsing strategy guarantees uniform therapy dose over the treatment volume at all times during treatment. In FIG. 5, steered focal locations for the 219 foci are shown with alternating 1 mm spaced grids of 7×7 foci and 6×6 foci.

The axial layers are separated by 1 mm, but with the 6×6 grids offset laterally from the 7×7 layers by 0.5 mm.

Figure 6:
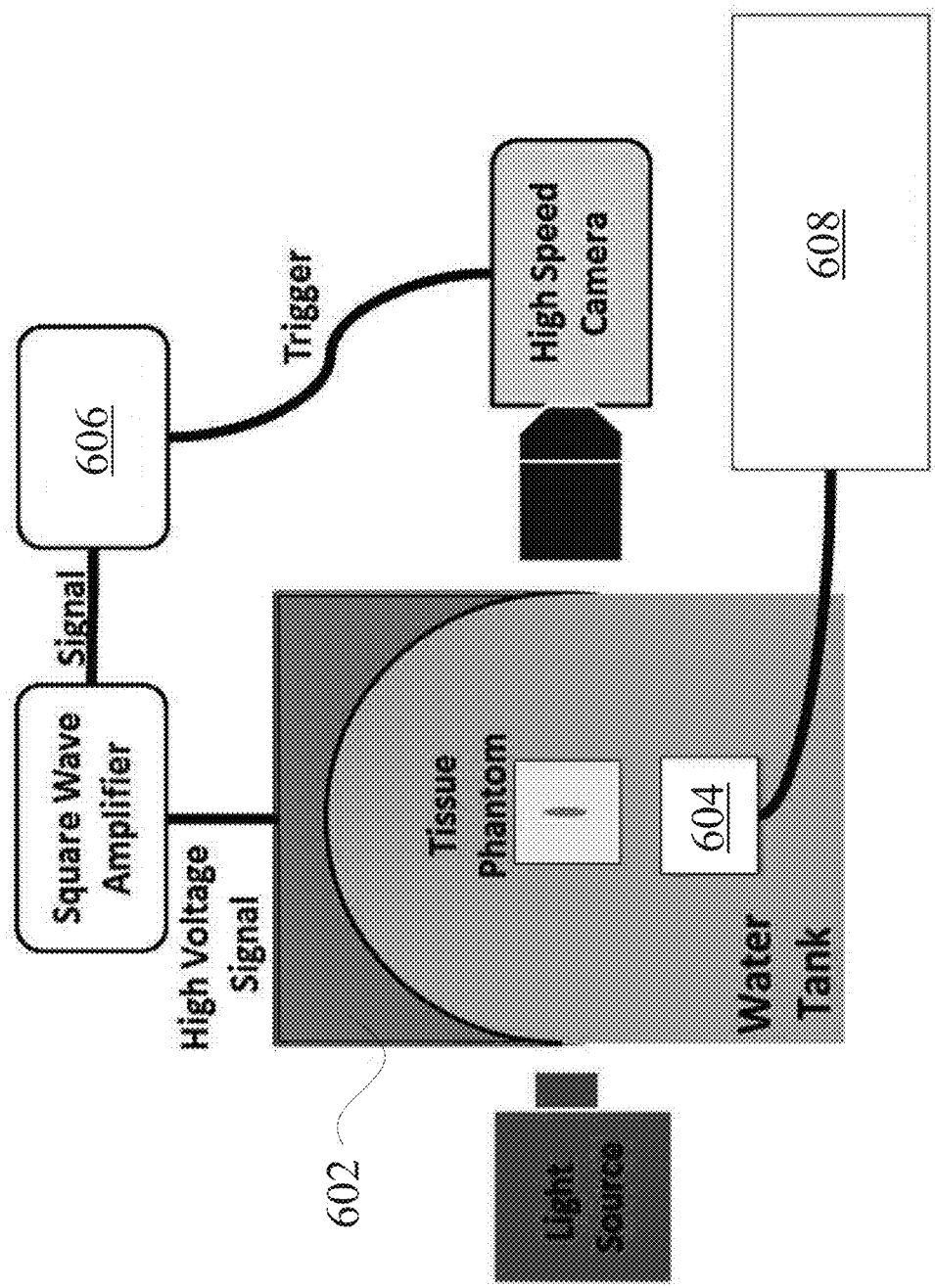
FIG. 6: Experimental setup with 500 kHz transducer mounted to the side of a water tank with 5 MHz imaging probe mounted opposite the therapy and aligned along the therapy axis. The Phantom high speed camera was positioned perpendicular to the therapy axis.

The internal memory of the high-speed camera may not be able to accommodate acquisitions after every pulse, so to facilitate continuous treatment without interruptions for data transfer; images can be captured periodically (e.g., after every 10$^{th}$ pulse delivered to the center focal location). Ultrasound Doppler acquisitions can be performed after every therapy pulse. The imaging transducer can be positioned opposite the therapy transducer, as described above, aligned along the therapy axis, i.e., the ultrasound imaging beam can be rigidly aligned with the therapy beam to avoid the effect of angle variation on Doppler. An experimental setup is illustrated in FIG. 6, which shows a therapy transducer 602, a Doppler imaging transducer 604, ultrasound control system 606, and imaging control system 608. The experimental setup also shows the tissue phantom disposed in a water tank and a high speed camera and light source for additional imaging capabilities. In one embodiment, the experimental setup included a 500 kHz transducer mounted to the side of a water tank with 5 MHz imaging probe mounted opposite the therapy and aligned along the therapy axis. The high speed camera was positioned perpendicular to the therapy axis.

In the experiment, a tissue-mimicking agarose gel phantom with an embedded red blood cell (RBC) layer was used to visualize and quantify the development of the lesion. These phantoms have been shown to produce reliable estimates of the cavitation-induced damage zone resulting from Histotripsy therapy. In this phantom, the RBC area lysed by Histotripsy changed from opaque red to translucent pink, allowing direct visualization and quantification of the lesion development. The lesions were photographed during treatment after each application of the 219 focal patterns. Simultaneous ultrasound Doppler acquisitions were also performed for direct comparison. The average pixel intensity within the lesion was then computed over the course of the treatment as a direct quantification of the fractionation progression in the tissue phantom and compared to the measured Doppler velocity progression.

An experiment was conducted in ex vivo porcine liver to analyze the color Doppler monitoring of the Histotripsy fractionation progression in tissue and compare it to the results from the agarose phantom. This experiment used an identical setup as above, with the agarose gel tissue phantom replaced with a freshly harvested piece of porcine liver tissue, degassed and embedded in 1% agarose gel and positioned over the geometric focus.

The liver was treated with 2000 pulses at each of the 219 focal locations, with ultrasound Doppler acquisitions performed after every pulse delivered to the center focal location. High-speed optical imaging for PIV analysis was not possible in the tissue.

The high-speed optical images of the focal region were processed to estimate the motion resulting from the Histotripsy therapy pulses. The PIV analysis was performed in a ~1.7 by 0.85 mm field of view at a resolution of 151 pixels per mm (total 256×128 pixels at 50 kHz frame rate) for the glass bead layer experiments and ~6.6 by 3.3 mm field of view at a resolution of 116 pixels per mm (total 768×384 pixels at 10 kHz frame rate) for the large lesion treatments. The images were processed in pairs at two subsequent time points using a FFT window deformation algorithm with 3 pass velocity estimation with image block sizes and step sizes of 24/12 pixels for pass 1, 16/8 pixels for pass 2, and 8/4 pixels for pass 3 in the glass bead layer experiment and 64/32 pixels for pass 1, 32/16 pixels for pass 2, and 16/8 pixels for pass 3 in the larger lesion treatments. Both resulted in velocity field maps of the field of view over the 19 ms after a Histotripsy therapy pulse. The axial components of these PIV velocity maps were then averaged over the bubble cloud area to produce the final average velocity estimate over time.

The ultrasound Doppler acquisitions were also processed. To calculate the velocity over the 19 ms after the therapy pulse, the 200 acquisitions were processed in rolling 10 acquisition segments (equivalent to using 10 frames at 10 kHz PRF, with different delay times after the histrispy pulse). These Doppler velocity maps were then averaged over the 2×4 mm bubble cloud area to produce the final average velocity estimate over time.

Figure 7A:
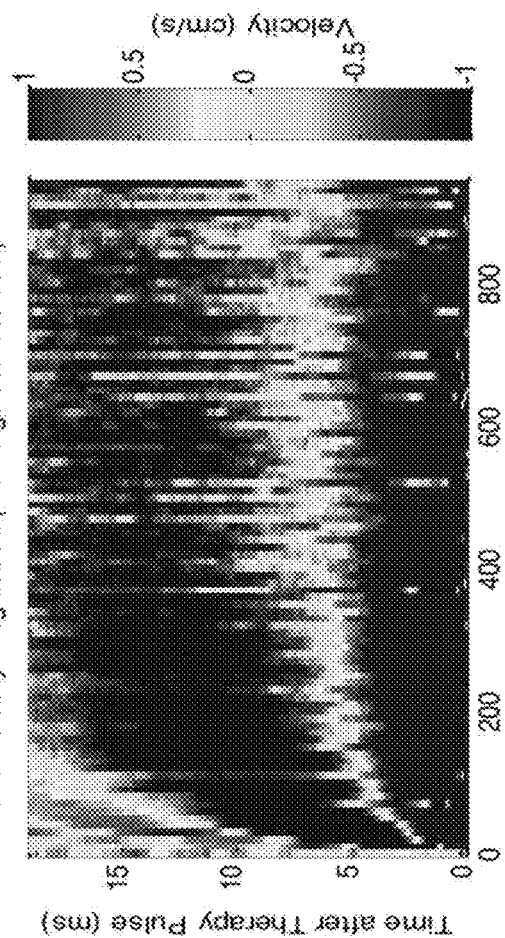
FIGS. 7A-7B: Plots showing the velocity estimates from PIV (top) and Doppler (bottom) after every 10 therapy pulses.
Figure 7B:
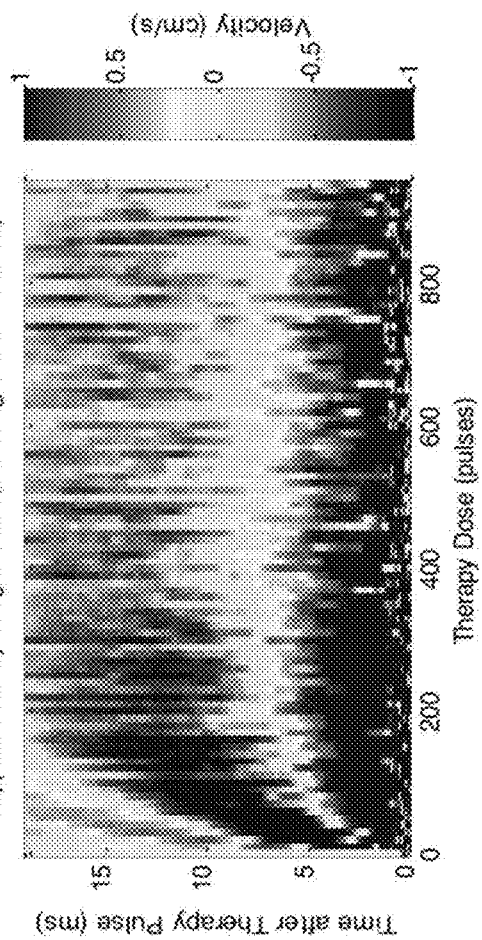

The full velocity profiles over the 960 pulse treatments are shown in FIGS. 7A-7B for both PIV (FIG. 7A) and Doppler (FIG. 7B) estimation methods. The estimated velocity is shown versus the delay from the therapy pulse (y axis) and the therapy dose (x axis).

Figure 8:
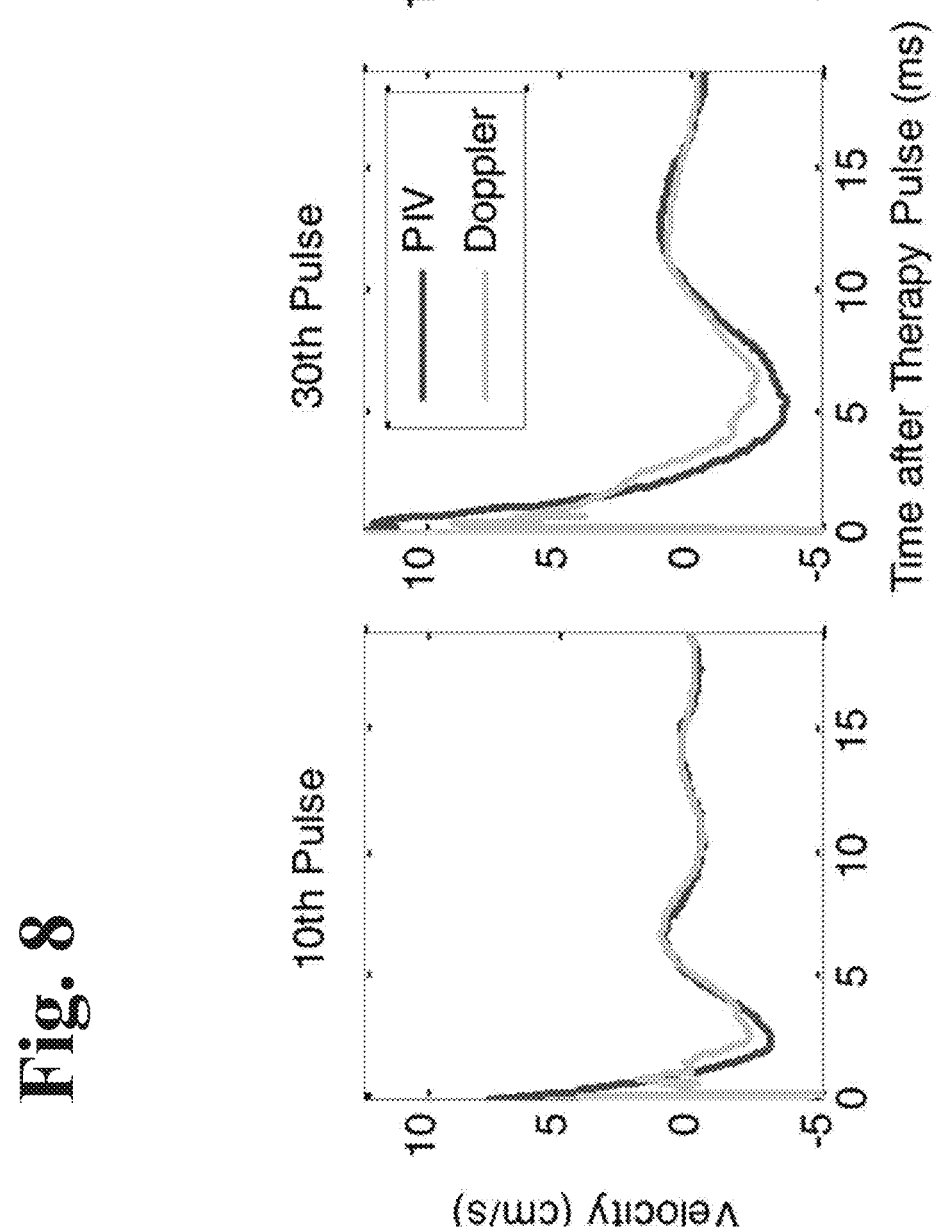
FIG. 8: Individual velocity plots for the 19 ms after the therapy pulse after 10 therapy pulses (left), 30 therapy pulses (center), and 290 therapy pulses (right) showing good agreement between PIV and Doppler in measured velocity after the initial chaotic motion.

FIG. 8 shows 3 individual velocity traces after 10, 30, and 290 therapy pulses. After the chaotic motion phase, PIV and Doppler estimates agree with each other well over the course of treatment. These plots show a time expansion of the velocity profile with increased therapy dose, which is likely due to the elasticity decrease as the phantom when it was gradually fractionated by Histotripsy pulses. The increase in the duration of the coherent push and rebound motion reached a peak after 400 pulses, likely because the phantom was completely liquefied. FIG. 8 shows good agreement between PIV and Doppler in measured velocity after the initial chaotic motion.

Figure 9:
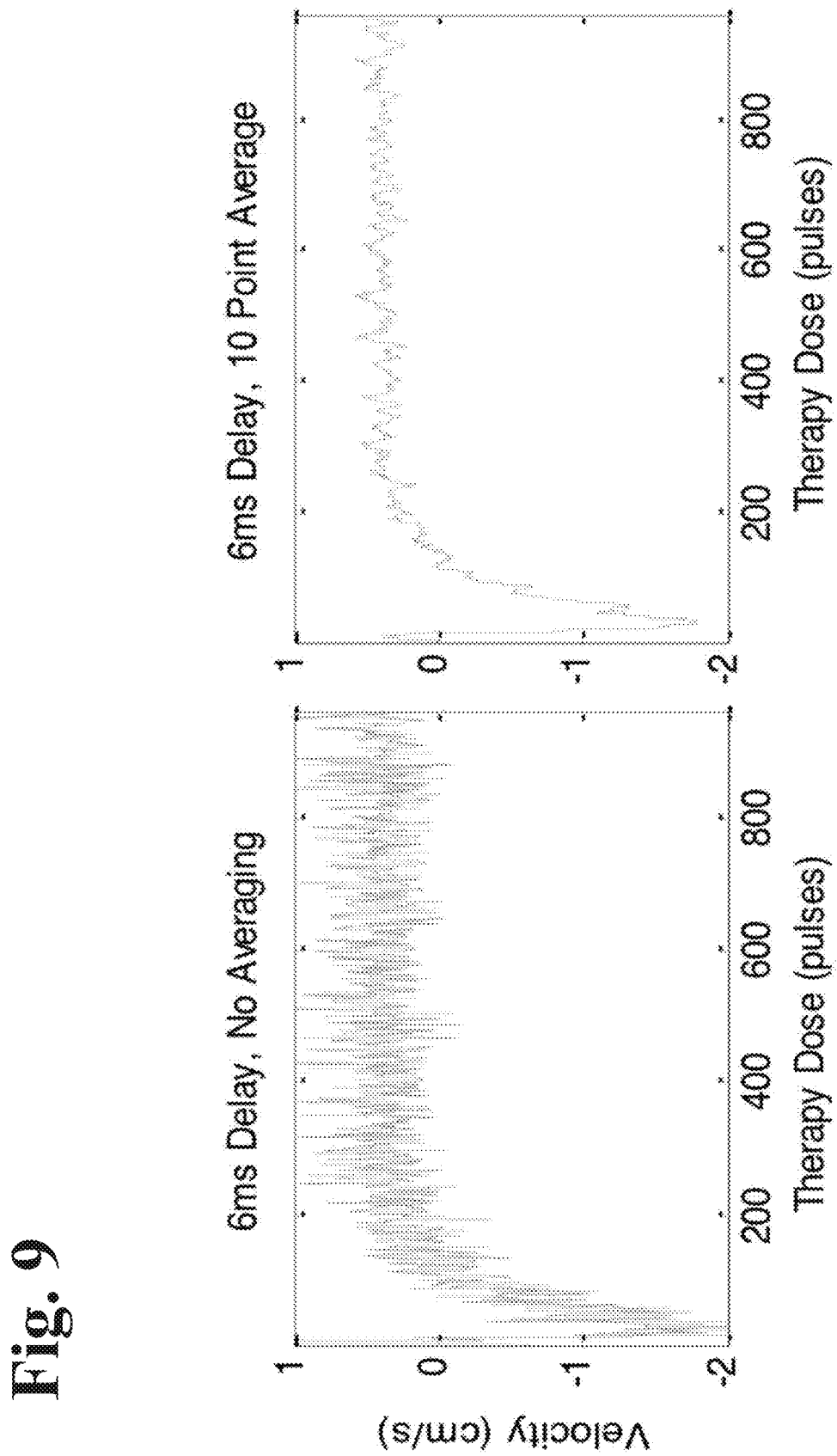
FIG. 9: Doppler velocity progression at a 6 ms delay from therapy pulse without averaging (left) and with a 10 pulse running average (right).

The velocity progression at any single delay between the Histrispy pulse and the Doppler pulse packet can be extracted from this dataset, producing the average velocity within a 1 ms window over the course of therapy. These velocity progressions are readily attainable in real-time from color Doppler during Histotripsy therapy, with an average processing frame rate around 30 Hz. The Doppler velocity progression at 6 ms delay from the Histotripsy pulse is shown in FIG. 9. In this case, the Doppler measurement estimates the average velocity during the time window from 6-7 ms after the therapy pulse. During this window, the velocity started at a positive value (first 15 pulses), then changed to a negative value (pulses 15-140), then became positive again (after 140 pulses), and eventually stabilized at a positive velocity after 260 pulses. These changes provide real-time feedback on fractionation progression during Histotripsy therapy, even indicating complete fractionation of the agarose tissue phantom when the velocity measurement peaks. FIG. 9 shows Doppler velocity progression at a 6 ms delay from therapy pulse without averaging (left) and with a 10 pulse running average (right).

Figure 10:
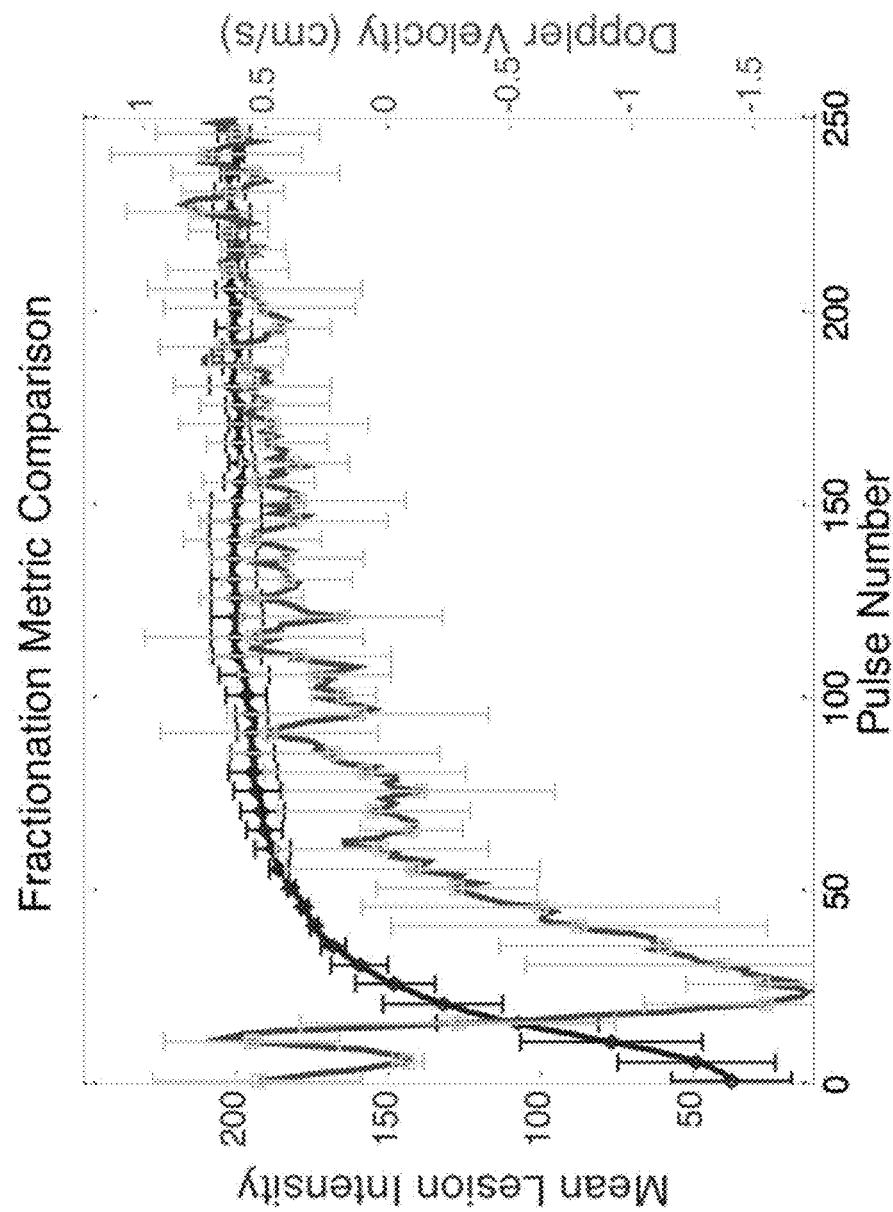
FIG. 10: A comparison of the Doppler velocity fractionation metric versus the mean lesion intensity metric in the damage indicating RBC layer (N=6). Both Doppler velocity and the lesion progress rapidly increased until ~100 pulses.

FIG. 10 shows a comparison of the Doppler velocity fractionation metric versus the mean lesion intensity metric in the damage indicating RBC layer (N=6). Both Doppler velocity and the lesion progress rapidly increased until ~100 pulses. In the agarose tissue phantom containing the damage indicating red blood cell (RBC) layer, the pixel intensity within the lesion increased with increased therapy dose, saturating after approximately 100 pulses. The Doppler velocity at a 6 ms delay was observed to change rapidly during this time period until 100 pulses. The Doppler velocity continued to change at a slower rate beyond this point before saturating after approximately 200 pulses.

Figure 11:
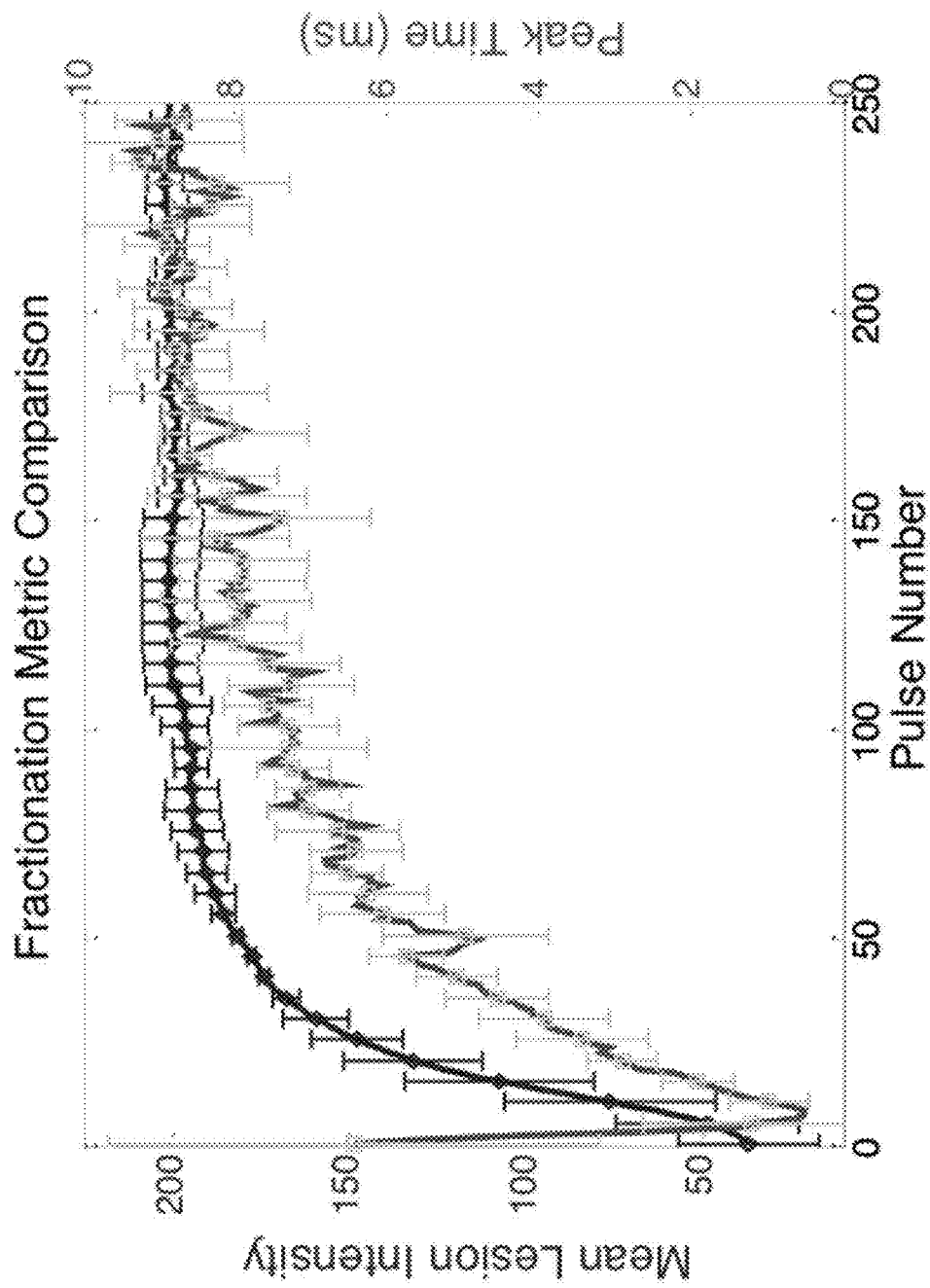
FIG. 11: Alternative progression metric, time to peak velocity, shows less variation and captures the same rapid change up to 100 pulses shown in the mean lesion intensity, with a slower continued progression up to 200 pulses.

This Doppler velocity metric is obtainable in real-time at high frame rates (up to 200 Hz) during Histotripsy therapy, however if high frame rates are not required, alternative metrics are also possible. For example, the time to peak velocity shown in FIG. 11 also captures the same rapid change up to 100 pulses observed in the lesion intensity, and also the continued slow increase up to 200 pulses. In FIG. 11, an alternative progression metric, time to peak velocity, shows less variation and captures the same rapid change up to 100 pulses shown in the mean lesion intensity, with a slower continued progression up to 200 pulses.

Figure 12:
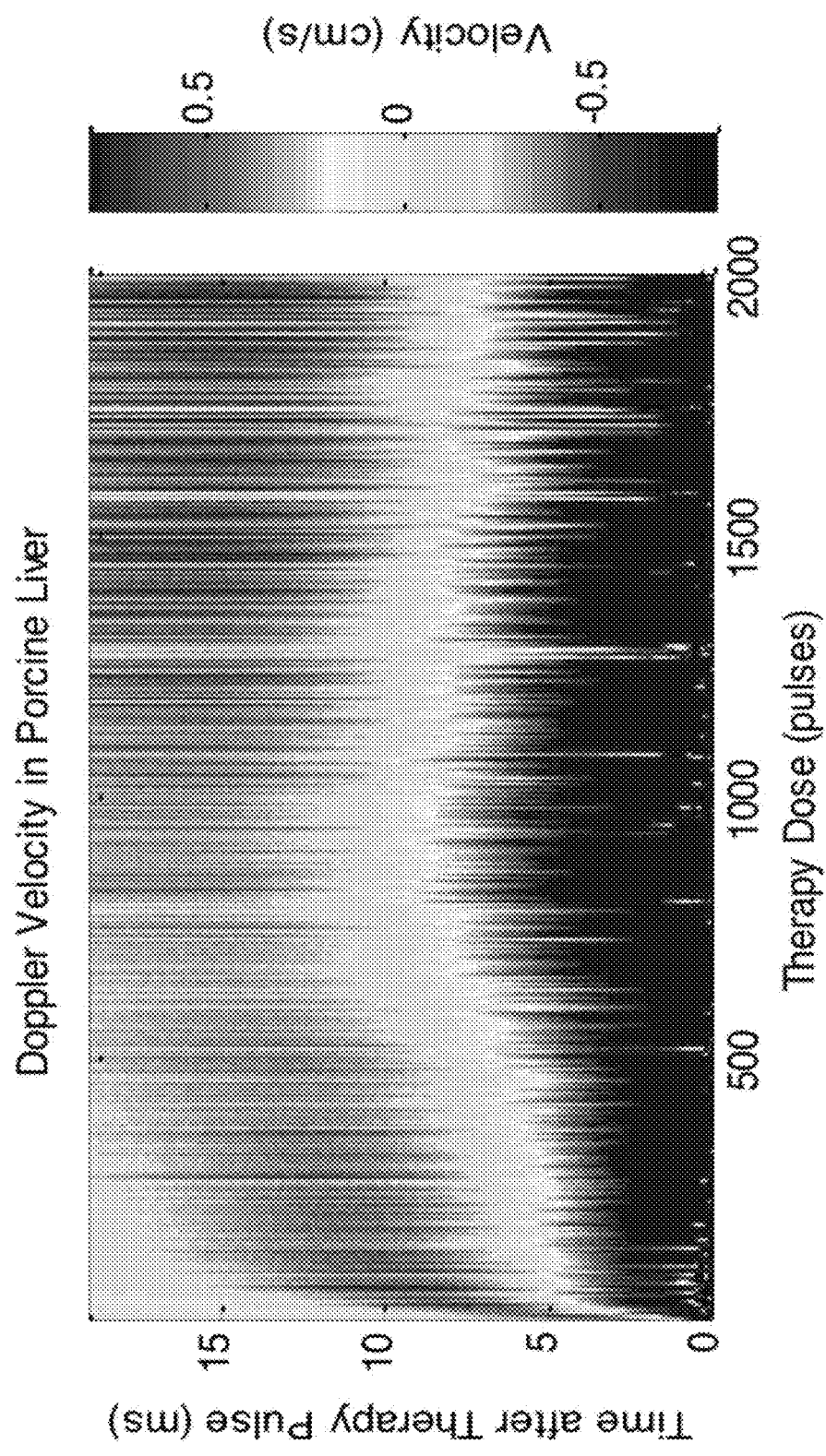
FIG. 12: Plot showing the velocity estimates from Doppler after every therapy pulse in ex vivo porcine liver.

In the ex vivo porcine liver, velocity profiles were collected after each of 2000 therapy pulses at the center of the treated volume. FIG. 12 shows the full velocity profile over the entire treatment. The estimated velocity is shown versus the delay from the therapy pulse (y axis) and therapy dose (x axis). The Doppler velocity profiles in the ex vivo porcine liver were similar to the agarose phantom, with a brief period of chaotic motion followed by coherent motion. These coherent motions also expanded in time with increased therapy dose very rapidly up to 50 pulses. After 50 pulses, the temporal profile of the Doppler velocity continued to expand at a slower rate until 900 pulses. After that point, the temporal profile of the Doppler velocity decreased slowly with increasing number of therapy pulses.

Figure 13:
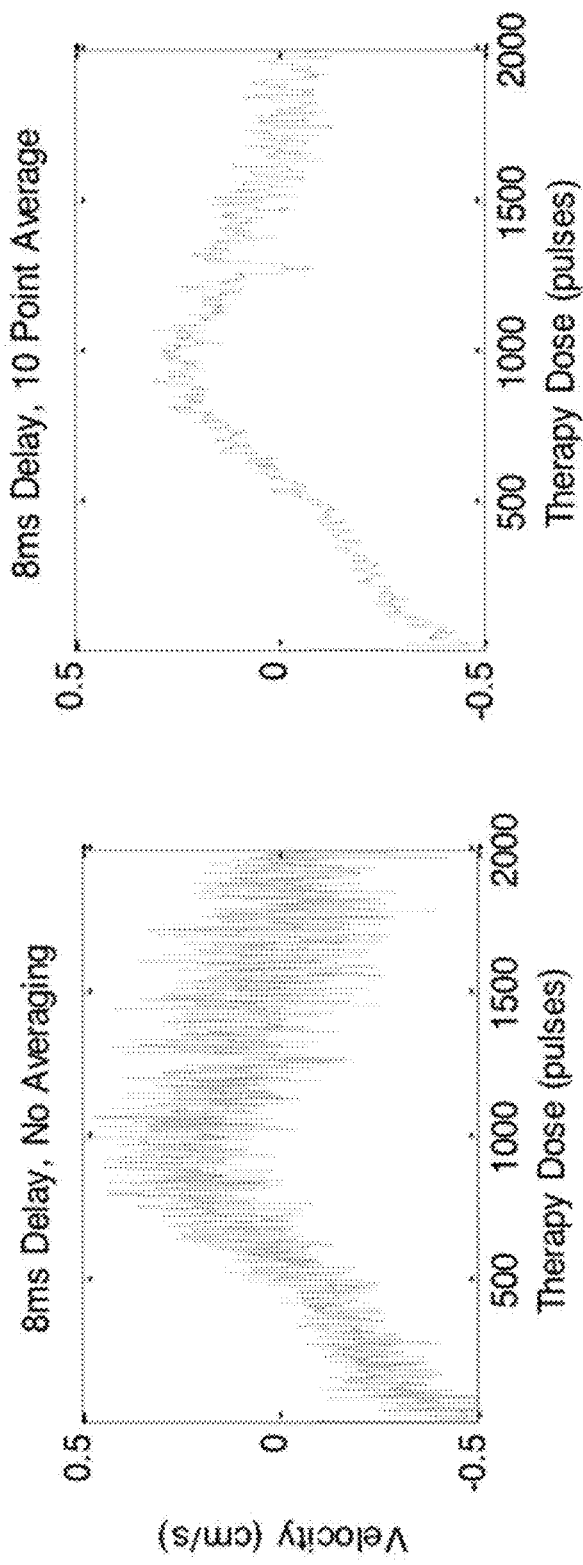
FIG. 13: Doppler velocity progression in ex vivo liver without averaging (left) and with a 10 point running average (right).

The velocity progression at a single delay of 8 ms was extracted from this dataset, producing the average velocity during the 8-9 ms window over the course of therapy. This is shown in FIG. 13. During this window the velocity increased quickly for the first 50 pulses, and then steadily at a slower rate up to 900 pulses as the tissue was fractionated. After 900 pulses, the velocity decreased steadily with increased variation from pulse to pulse. In FIG. 13, Doppler velocity progression in ex vivo liver is shown without averaging (left) and with a 10 point running average (right).

Figure 14:
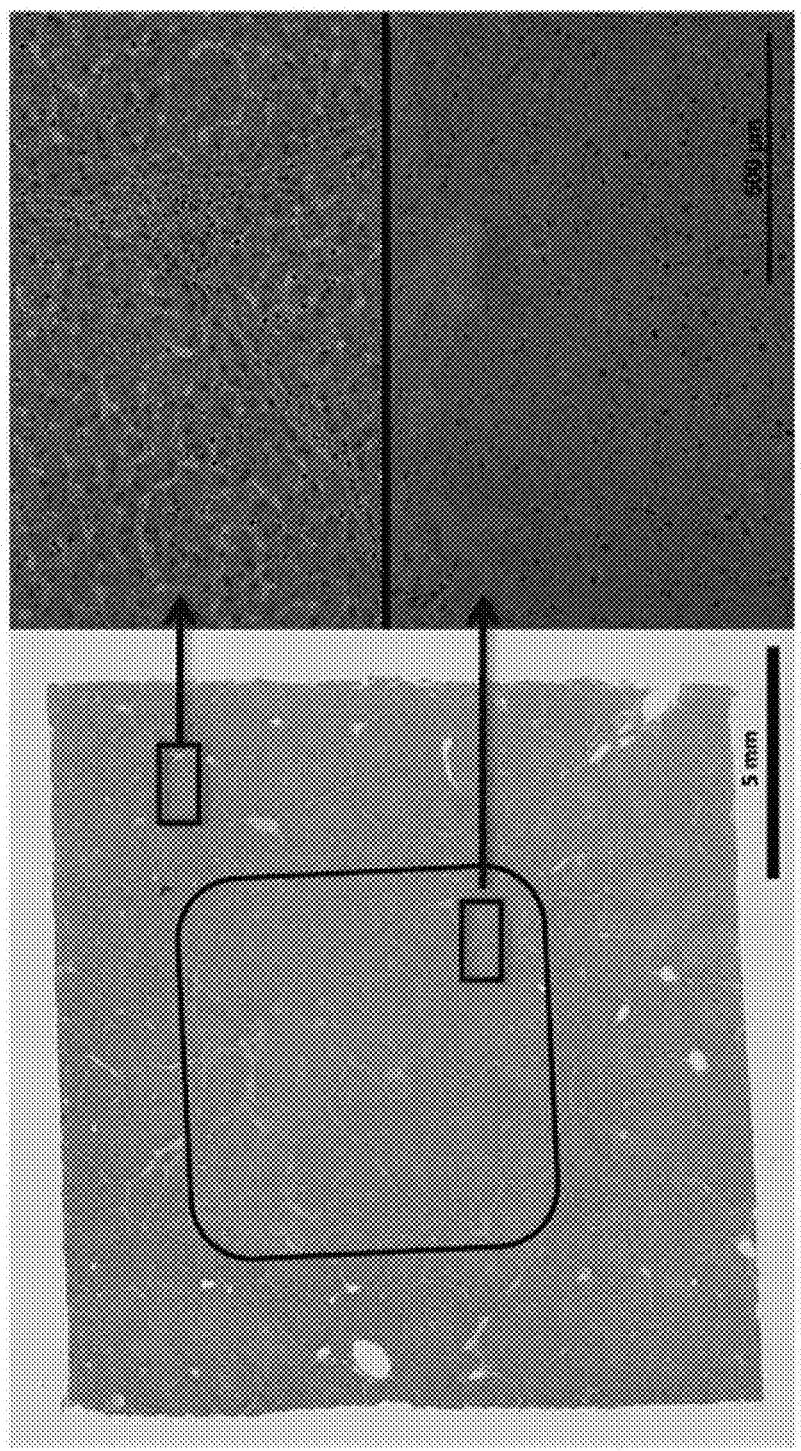
FIG. 14: Histological images of the lesion after 50 therapy pulses. Macroscopic image (left) shows little large-scale homogenization, however widespread mechanical fractionation is visible microscopically (bottom right) compared to control (top right).

Histological analysis was completed on separate lesions after 50, 200, and 500 pulse treatments to visualize the lesion progression in the tissue resulting from these treatment parameters. FIG. 14 shows the lesion resulting from a 50 pulse treatment, with widespread mechanical disruption of the cellular structures visible microscopically in the entire treatment region. This widespread microscopic cellular damage is sufficient to cause tissue death. No macroscopic homogenization of the tissue structure was visible after 50 pulses. In FIG. 14, Histological images of the lesion after 50 therapy pulses are shown. The macroscopic image (left) shows little large-scale homogenization, however widespread mechanical fractionation is visible microscopically (bottom right) compared to control (top right).

Figure 15:
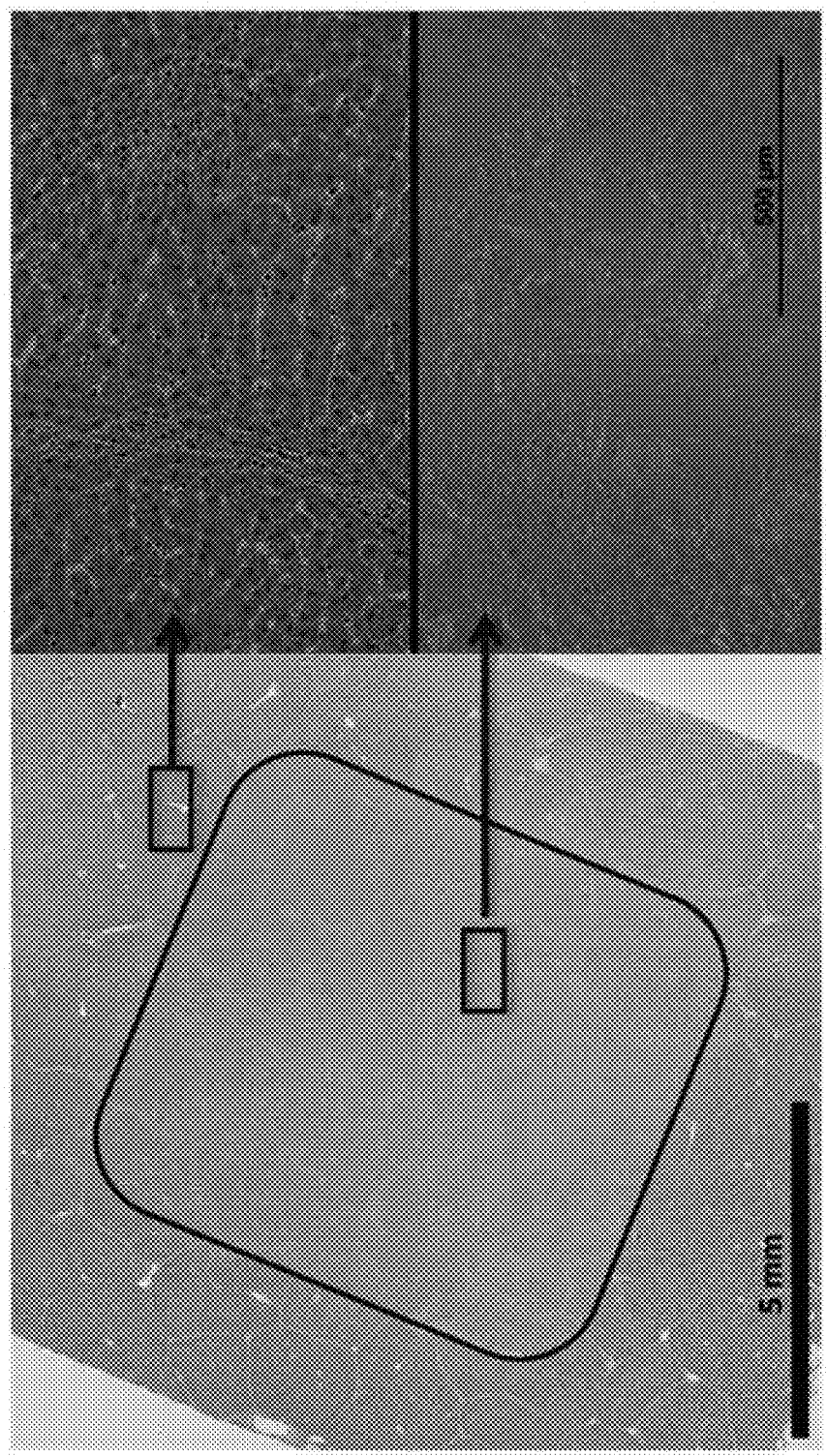
FIG. 15: Histological images of the lesion after 200 therapy pulses. Macroscopic image (left) shows clear large-scale homogenization, with increased mechanical fractionation visible microscopically (bottom right) compared to control (top right).

After 200 pulses however, fractionation to the macroscopic tissue structure is much more evident, with a nearly homogeneous appearing lesion as shown in FIG. 15. Microscopically, increased fractionation of cellular structure and nuclei is apparent, along with increased homogeneity and mixing of fractionation products. In FIG. 15, histological images of the lesion are shown after 200 therapy pulses. Macroscopic image (left) shows clear large-scale homogenization, with increased mechanical fractionation visible microscopically (bottom right) compared to control (top right).

Figure 16:
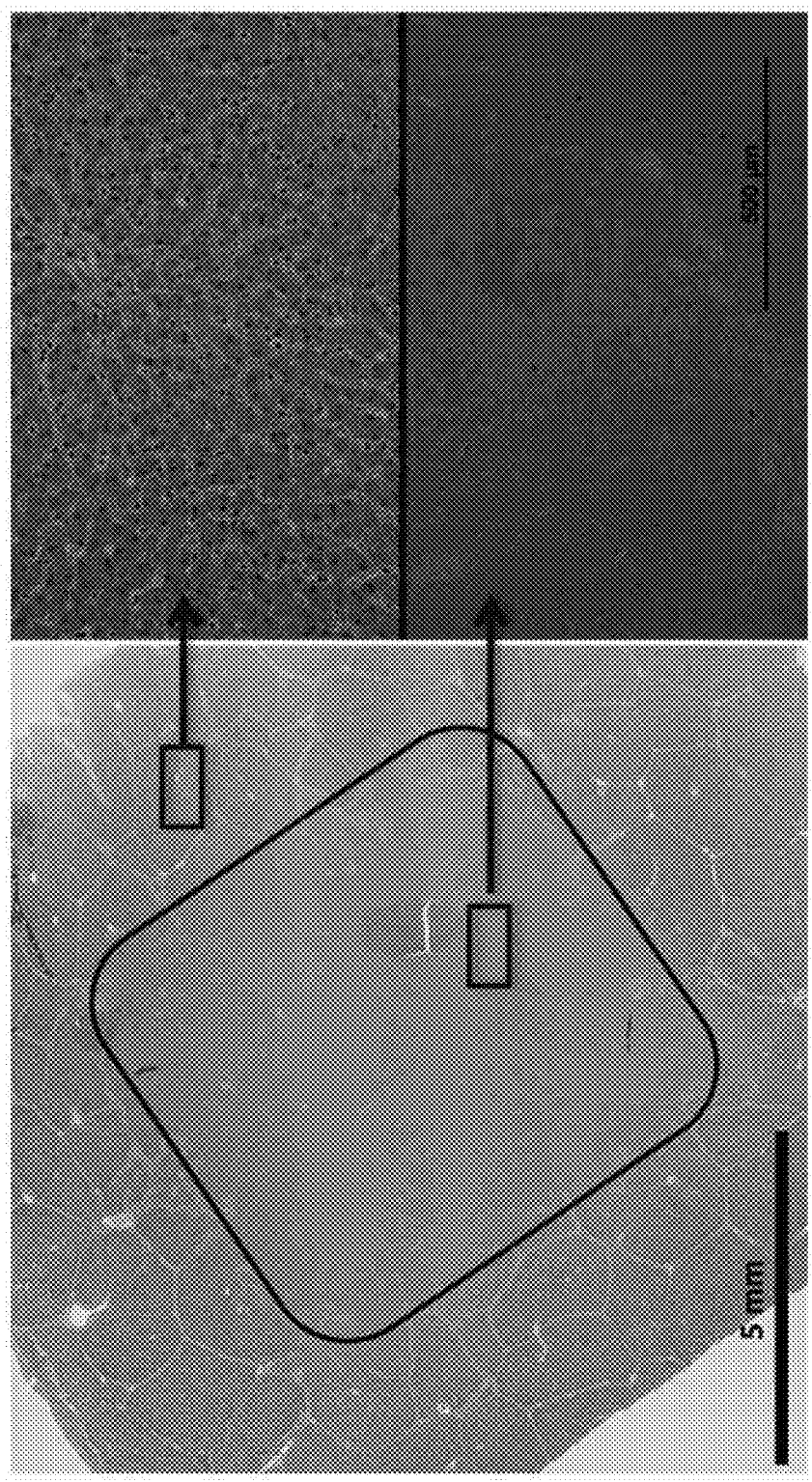
FIG. 16: Histological images of the lesion after 500 therapy pulses. Macroscopic image (left) shows complete large-scale homogenization, with near complete homogenization visible microscopically as well (bottom right) compared to control (top right).

After 500 pulses, as shown in FIG. 16, the lesion appears homogeneous and completely fractionated, with very few remaining cell nuclei in the homogenous fractionated tissue product. In FIG. 16, histological images of the lesion are shown after 500 therapy pulses. The macroscopic image (left) shows complete large-scale homogenization, with near complete homogenization visible microscopically as well (bottom right) compared to control (top right).

Comparing the Doppler velocity results and histology results, the initial rapid expansion in the temporal profile of the Doppler velocity match well with the microscopic cellular damage to the treated tissue, both were observed at 50 pulses. After that, the temporal profile of the Doppler velocity continues to expand, but the rate is more gradual. Correspondingly, macroscopic damage to the tissue structure is observed. When the tissue is completely liquefied with no tissue or cellular structures remaining, the temporal profile of the Doppler velocity flattens and begins to shrink at a very slow rate.

The bubble-induced color Doppler provides a real-time, high sensitivity feedback to monitor Histotripsy tissue fractionation during treatment. In comparison to the reduced echogenicity in the treatment zone (speckle amplitude reduction) currently used in monitoring Histotripsy tissue fractionation, the bubble-induced color Doppler feedback can predict microscopic cellular damage, especially at an earlier treatment stage, which cannot be achieved with reduced echogenicity. Moreover, bubble-induced color Doppler has the potential to predict microscopic cellular damage versus the macroscopic damage to the tissue structure. This level of sensitivity is very important for clinical application to predict the end point for treatment for different clinical applications.

The bubble-induced color Doppler can provide consistent and reliable feedback across different tissues and patients. Our data suggest that the slope or the rate of Doppler velocity change, either the temporal profile of the velocity within sub-time window of the coherent motion, can be used to monitor the treatment, to detect microscopic cellular damage as well as macroscopic tissue structure homogenization. The detection does not depend on the absolute value of the Doppler velocity that may vary across patients, but the relative change, and therefore is expected to be consistent and reliable across different organs and patients.

The bubble-induced color Doppler can be displayed as color overlaid on gray-scale ultrasound images, providing a high contrast feedback to monitor the degree of tissue fractionation (i.e., treatment progress and completion). Such feedback is unambiguous and easy to use even for inexperienced users.

As described above, an ultrasound imaging transducer can be placed in-line (or co-axially) with the Histotripsy therapy transducer. For example, such configuration can be achieved by having a small center hole in the therapy transducer to house the imaging probe. The Doppler acquisition on the ultrasound imaging system needs to be synchronized by the Histotripsy therapy pulse such that the first Doppler pulse arrives at the focus at a predefined delay time after the arrival of the Histotripsy pulse.

For the speckle amplitude reduction approach currently used to monitor Histotripsy tissue fractionation, the speckle amplitude has been observed to increase back shortly after treatment likely due to the coagulation of the fractioned region, causing the speckle reduction approach ineffective. However, even with the coagulation, the change in tissue elasticity from tissue fractionation remains substantial and should still be usable in the presence of coagulation.

As Doppler is an important tool in evaluating cardiovascular function clinically, the real-time bubble-induced color Doppler should also allow evaluation of the vessel or the heart close to the treatment target during the Histotripsy treatment. Different colors can be used for tissue motion (e.g., green and yellow) to distinguish from the red and blue commonly used in color Doppler for blood flow.

The ultrasound gray-scale imaging quality of deep tissue (e.g., deep internal organs) is often degraded significantly due to the attenuation and aberration from the overlying tissue, resulting in coarse tissue speckle and making the accurate tissue motion tracking difficult. However, the residual nuclei from bubble cloud generated by Histotripsy last over 100 milliseconds after each Histotripsy pulse and moves with the target tissue, providing strong ultrasound speckles for motion tracking during bubble-induced color Doppler.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of monitoring Doppler-based feedback during Histotripsy treatment comprising the steps of:
    transmitting Histotripsy pulses into a target tissue to generate a cavitation bubble cloud in the target tissue, the Histotripsy pulses having a pulse length less than 50 µsec, a peak negative pressure greater than 10 MPa, and a duty cycle less than 5%;
    transmitting Doppler ultrasound imaging pulses into the target tissue after the cavitation bubble cloud collapses;
    monitoring a coherent motion along a direction of the transmitted Histotripsy pulses with the Doppler ultrasound imaging pulses;
    analyzing a Doppler velocity of the Doppler ultrasound imaging pulses to quantitatively predict a level of tissue fractionation in the target tissue in real-time; and
    displaying a Doppler velocity map to provide real-time imaging feedback of the tissue fractionation in the target tissue.

2. The method of claim 1 further comprising synchronizing the Histotripsy pulses and the Doppler ultrasound imaging pulses with a predetermined time delay.

3. The method of claim 1, further comprising determining that the target tissue is increasingly fractionated as the Doppler velocity changes.

4. The method of claim 1, further comprising determining that the target tissue is liquefied when the Doppler velocity saturates.

5. The method of claim 1 further comprising:
    displaying the Doppler velocity map as a colored region overlaid on a gray-scale image of the target tissue.

6. The method of claim 1 further comprising monitoring vessel function and cardiac function during transmission of the Histotripsy pulses.

* * * * *